(12) United States Patent
Medoff et al.

(10) Patent No.: US 9,328,393 B2
(45) Date of Patent: May 3, 2016

(54) PROCESSING BIOMASS

(75) Inventors: Marshall Medoff, Brookline, MA (US); Seul-a Bae, Arlington, MA (US); Randy Valdez, Boston, MA (US); Thomas Craig Masterman, Brookline, MA (US)

(73) Assignee: XYLECO, INC., Wakefield, MA (US)

( * ) Notice: Subject to any disclaimer, the term of this patent is extended or adjusted under 35 U.S.C. 154(b) by 0 days.

(21) Appl. No.: 13/491,797

(22) Filed: Jun. 8, 2012

(65) Prior Publication Data

US 2012/0315675 A1 Dec. 13, 2012

Related U.S. Application Data

(60) Provisional application No. 61/495,217, filed on Jun. 9, 2011.

(51) Int. Cl.

| | |
|---|---|
| C12P 1/00 | (2006.01) |
| C13K 1/06 | (2006.01) |
| C08H 8/00 | (2010.01) |
| C13K 1/02 | (2006.01) |
| B01F 5/02 | (2006.01) |
| B01F 5/10 | (2006.01) |
| B01F 7/00 | (2006.01) |
| B01F 7/16 | (2006.01) |
| B01F 15/00 | (2006.01) |
| B01F 3/12 | (2006.01) |
| C13K 13/00 | (2006.01) |
| C12P 19/02 | (2006.01) |
| C12P 19/14 | (2006.01) |
| C12M 1/00 | (2006.01) |
| C08J 3/28 | (2006.01) |
| C10G 32/00 | (2006.01) |
| C10G 1/00 | (2006.01) |

(52) U.S. Cl.
CPC ............... *C13K 1/06* (2013.01); *B01F 3/1271* (2013.01); *B01F 5/0212* (2013.01); *B01F 5/106* (2013.01); *B01F 7/00358* (2013.01); *B01F 7/1635* (2013.01); *B01F 15/00246* (2013.01); *C08H 8/00* (2013.01); *C08J 3/28* (2013.01); *C10G 1/00* (2013.01); *C10G 32/00* (2013.01); *C12M 45/09* (2013.01); *C12P 19/02* (2013.01); *C12P 19/14* (2013.01); *C13K 1/02* (2013.01); *C13K 13/002* (2013.01); *C08J 2301/02* (2013.01); *C10G 2300/1014* (2013.01); *C12P 2201/00* (2013.01); *C12P 2203/00* (2013.01); *Y02E 50/13* (2013.01); *Y02E 50/16* (2013.01); *Y02P 30/20* (2015.11)

(58) Field of Classification Search
USPC .......................................................... 435/155
See application file for complete search history.

(56) References Cited

U.S. PATENT DOCUMENTS

| | | | | |
|---|---|---|---|---|
| 3,654,081 | A | * | 4/1972 | Orville ............................ 435/99 |
| 5,498,766 | A | | 3/1996 | Stuart et al. |
| 5,677,154 | A | * | 10/1997 | Van Draanen et al. ........ 435/163 |
| 2005/0176000 | A1 | * | 8/2005 | Callen et al. ....................... 435/6 |
| 2009/0126274 | A1 | | 5/2009 | Vogel |
| 2011/0177558 | A1 | * | 7/2011 | Medoff et al. ................... 435/72 |
| 2012/0100577 | A1 | * | 4/2012 | Medoff ...................... C12P 7/10 |
| | | | | 435/72 |

FOREIGN PATENT DOCUMENTS

| | | | |
|---|---|---|---|
| SU | 1559026 A1 | 4/1990 | |
| WO | 9413838 | 6/1994 | |
| WO | WO 9505087 A1 * | 2/1995 | ........... A23K 1/1813 |
| WO | 2007044742 | 4/2007 | |
| WO | WO 2008073186 A2 * | 6/2008 | |
| WO | 2010093829 | 8/2010 | |
| WO | 2010135365 | 11/2010 | |
| WO | WO 2010135365 A2 * | 11/2010 | .............. C12M 21/12 |

OTHER PUBLICATIONS

Davis, Kelly S. Corn Milling, Processing and Generation of Co-Products. Minnesota Nutrition Conference. Minnesota Corn Growers Association. Sep. 11, 2001. pp. 1-7.*
Bak, Jin et al. Improved Enzymatic Hydrolysis Yield of Rice Straw Using Electron Beam Irradiation Pretreatment. Bioresource Technology. vol. 100, Issue 3. Elsevier. Feb. 2009. pp. 1285-1290.*
Sokhansanj, S et al. Biomass Densification—Cubing Operations and Costs for Corn Stover. Applied Engineering in Agriculture. 2004, vol. 20 No. 4. pp. 495-499.*
Gaspar, Melinda et. al. Corn Fiber as a Raw Material for Hemicellulose and Ethanol Production. Process Biochemistry 42 (2007). pp. 1135-1139.*
PCT Search Report—PCT/US2012/041382, dated Sep. 28, 2012.
Singapore Search Report, Corresponding Singapore Application No. 2013084538, dated Mar. 18, 2015, 3 pages.
Anonymous, "IKA Technology Contributes to the Optimal Use of Renewable Energy Sources," May 2011, retrieved on Apr. 27, 2015, Retrieved from the Internet: <URL: www.ikaprocess.com/Services/Downloads-cdc.html?iDiv=3&ilD=1>, 4 pages.

\* cited by examiner

*Primary Examiner* — Kagnew H Gebreyesus
*Assistant Examiner* — Nghi Nguyen
(74) *Attorney, Agent, or Firm* — Leber Patent Law P.C.

(57) ABSTRACT

Biomass feedstocks (e.g., plant biomass, animal biomass, and municipal waste biomass) are processed to produce useful products, such as fuels. For example, systems are described that can convert feedstock materials to a sugar solution, which can then be fermented to produce a product such as a biofuel.

22 Claims, 19 Drawing Sheets

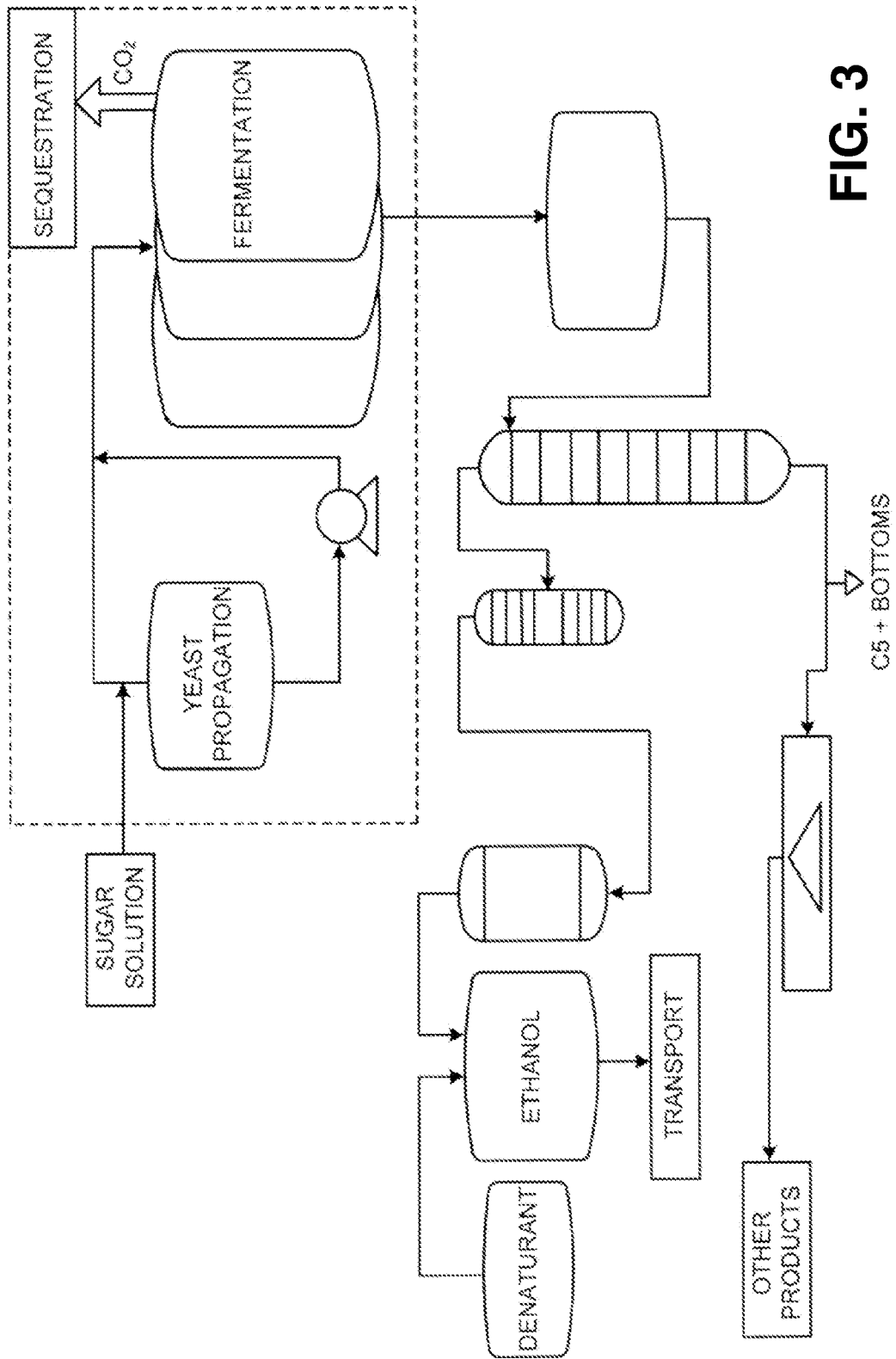

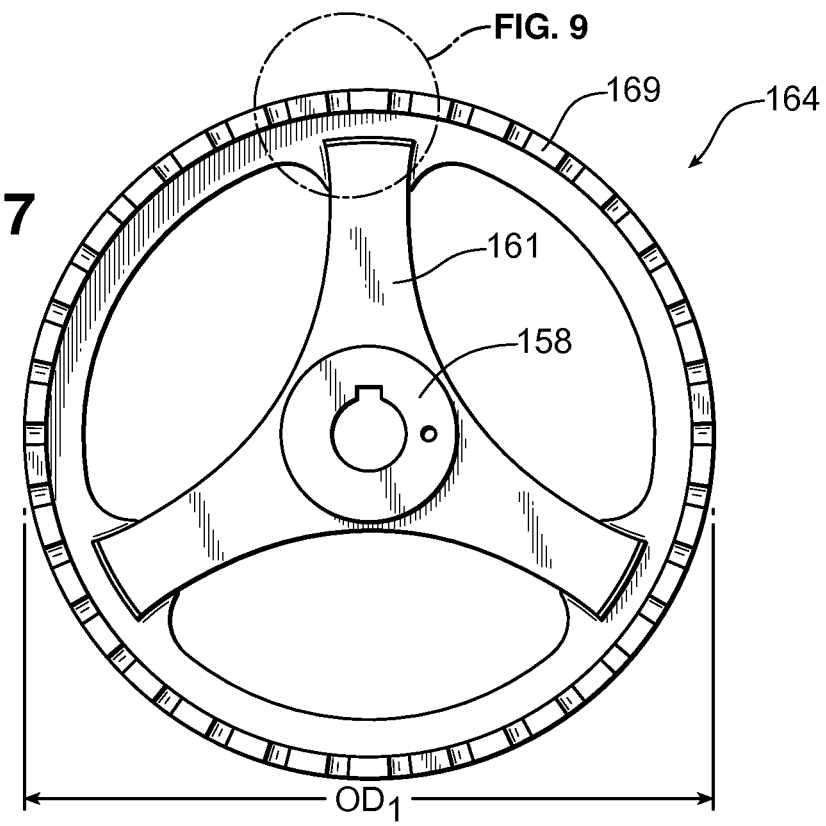
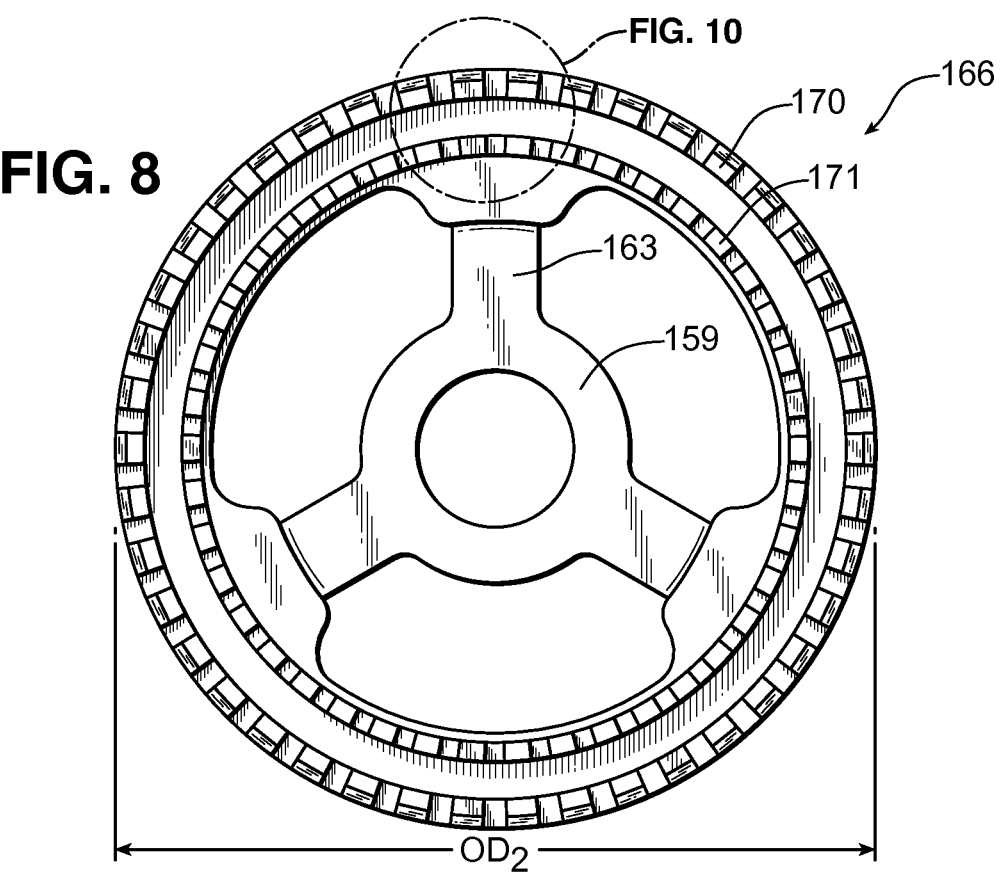

PROCESSING BIOMASS

RELATED APPLICATIONS

This application claims priority to U.S. Provisional Application Ser. No. 61/495,217, filed Jun. 9, 2011. The complete disclosure of this provisional application is hereby incorporated by reference herein.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

SUMMARY

Processes are disclosed herein for saccharifying or liquifying a biomass material, e.g., cellulosic, lignocellulosic and/or starchy feedstocks, by converting biomass material to low molecular weight sugars, e.g., saccharifying the feedstock using an enzyme, e.g., one or more cellulase and/or amylase. The invention also relates to converting a feedstock to a product, e.g., by bioprocessing, such as fermentation. The processes include wet milling a feedstock. The inventors have found that wet milling the feedstock tends to reduce the time required for saccharification, and increase the concentration of sugar that can be obtained in a given saccharification time. Wet milling alone or working synergistically with any treatment described herein can reduce recalcitrance of a biomass material.

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05. or less, e.g., less than 0.025 g/cm$^3$.

Such materials can be difficult to disperse in liquids, e.g., with water or a solvent system for saccharification, fermentation, or other processing. Due to their low bulk density, the materials tend to float on the surface of the liquid rather than being wetted out and dispersed into the liquid. In some cases, the materials can be hydrophobic, highly crystalline, or otherwise difficult to wet. At the same time, it is desirable to process the feedstock in a relatively high solids level dispersion, in order to obtain a high final concentration of sugar in the saccharified material, or a high concentration of the desired product after processing (e.g., of ethanol or other alcohol(s) after fermentation). In some cases, utilizing the methods described herein the solids level of the dispersion during processing can be, for example, at least 10, 15, 20, 22.5, 25, 27.5, 30, 35, 40, 45, or even at least 50 percent by weight dissolved solids. For example, the solids level can be from about 10 to 50%, e.g., about 10-40%, 10-30%, or 10-20%.

In one aspect, the invention features reducing the particle size of a lignocellulosic material to less than 3000 μm, e.g. less than 2000 μm, less than 1000 μm or even less than 500 μm, e.g., less than 250 μm or less than 100 μm. The particle size range can be between 100-3000 μm, e.g., 200-2000 μm, 200-1000 μm, 500-1000 μm.

In one aspect, the invention features reducing recalcitrance of a lignocellulosic material and wet milling the lignocellulosic material. In some cases, recalcitrance is reduced prior to wet milling. The material can be densified prior to reducing the recalcitrance or after reducing the recalcitrance and prior to wet milling the material.

In another aspect, the invention features a method comprising wet milling a lignocellulosic material, e.g., a lignocellulosic material having a reduced recalcitrance.

Either of these aspects of the invention can include, in some implementations, any of the following features.

The recalcitrance of the biomass material, e.g., a lignocellulosic material, can be reduced, for example, by irradiating the lignocellulosic material, e.g., by exposing the material to an electron beam. In some cases, irradiating comprises delivering a dose of at least 5 Mrad to the lignocellulosic material, e.g., at least 10, 20, 30, 50, 100, 150 or even 200 Mrad. For example, doses can be in the range of 5-200 Mrad, e.g., 5-100 Mrad, 5-50 Mrad, 5-10 Mrad, 10-100 Mrad, or 10-50 Mrad.

The lignocellulosic material may be, for example, a material is selected from the group consisting of wood, particle board, sawdust, agricultural waste, sewage, silage, grasses, rice hulls, bagasse, cotton, jute, hemp, flax, bamboo, sisal, abaca, straw, wheat straw, corn cobs, corn stover, switchgrass, alfalfa, hay, coconut hair, seaweed, algae, and mixtures thereof.

The biomass may also be combinations of starchy, lignocellulosic and/or cellulosic materials. For example, a biomass can be an entire plant or part(s) of a plant e.g., a wheat plant, cotton plant, a corn plant, rice plant or a tree.

In some implementations, wet milling is performed using a rotor/stator head. The rotor and stator may include nesting rings of teeth. In some cases, the stator comprises two or more concentric rings of teeth, and the rotor comprises a ring of teeth configured to fit between adjacent rings of teeth of the stator. The clearance between the rotor and stator is generally small, to generate high shear, and may be, for example from about 0.01 to 0.25 inches (0.25 to 6.4 mm). The spacing between the teeth in each ring of teeth is also generally small, e.g., from about 0.1 to 0.3 inch (2.5 to 7.6 mm).

Wet milling may be performed using a plurality of rotor/stator heads, e.g., when the process is performed in a large tank or vessel.

Wet milling is generally performed at a relatively high shear rate. The shear rate may be, for example, at least 20,000 sec$^{-1}$, (e.g., at least 25,000 sec$^{-1}$, at least 30,000 sec$^{-1}$, at least 40,000 sec$^{-1}$ or at least 50,000 sec$^{-1}$). The shear rate can be, for example from about 30,000 sec$^{-1}$ to about 50,000 sec$^{-1}$ (e.g., from about 25,000 sec$^{-1}$ to about 50,000 sec$^{-1}$, from about 30,000 sec$^{-1}$ to about 50,000 sec$^{-1}$, from about 35,000 sec$^{-1}$ to about 50,000 sec$^{-1}$, from about 40,000 sec$^{-1}$ to about 50,000 sec$^{-1}$, from about 20,000 sec$^{-1}$ to about 45,000 sec$^{-1}$, from about 20,000 sec$^{-1}$ to about 40,000 sec$^{-1}$, from about 20,000 sec$^{-1}$ to about 30,000 sec$^{-1}$, from about 30,000 sec$^{-1}$ to about 40,000 sec$^{-1}$).

In some implementations, wet milling is performed in-line. A jet mixer may be applied during wet milling. The jet mixer may also be used during subsequent processing, e.g., during fermentation. The method may further include adding an enzyme to the biomass material, e.g., a lignocellulosic material, before, during or after wet milling, and/or adding a microorganism to the biomass material or a sugar derived from the biomass material. In some cases, the microorganism is added after wet milling has been completed, e.g., to avoid damage to the microorganism from wet milling. In some implementations, the microorganism converts the biomass feedstock or sugar to a product selected from the group consisting of alcohols, organic acids, sugars, hydrocarbons, and mixtures thereof.

The methods described herein generally provide relatively rapid and effective processing of a relatively high solids level of feedstock. By increasing the initial solids level of feedstock in the mixture, the process can proceed more rapidly, more efficiently and more cost-effectively, and a high resulting concentration can generally be achieved in the final product. In some cases, solids may be removed during saccharification, e.g., by a centrifuge, and more feedstock may be added. The removed solids may be used as a product, e.g., as a combustible fuel for cogeneration of electricity and/or as an animal feed.

The saccharification processes described herein allow biomass material, e.g., a cellulosic or lignocellulosic feedstock, to be converted to a convenient and concentrated form which can be easily transported and utilized in another manufacturing facility, e.g., a facility configured to ferment sugar solutions to alcohols, to manufacture a product, e.g., a fuel such as ethanol, butanol or a hydrocarbon. Such concentrates can use less water, which can result in substantial manufacturing and transportation cost savings.

Some processes disclosed herein include saccharification of the feedstock, and transportation of the feedstock from a remote location, e.g., where the feedstock is produced or stored, to the manufacturing facility. In some cases, saccharification can take place partially or entirely during transport.

In some cases, the systems described herein, or components thereof, may be portable, so that the system can be transported (e.g., by rail, truck, or marine vessel) from one location to another. Such mobile processing is described in U.S. Ser. No. 12/374,549 filed Jan. 21, 2009 and International Application No. WO 2008/011598, the full disclosures of which are incorporated herein by reference.

Exemplary products that can be produced by employing the methods described herein include hydrocarbons, proteins, alcohols (e.g., a monohydric alcohols or a dihydric alcohols), such as ethanol, isobutanol, n-propanol or n-butanol, carboxylic acids, such as acetic acid, lactic acid, citric acid, propionic acid, succinic acid, 3-hydroxyproprionic acid or butyric acid, salts of a carboxylic acid, a mixture of carboxylic acids and salts of carboxylic acids and esters of carboxylic acids (e.g., methyl, ethyl and n-propyl esters), ketones, aldehydes, alpha unsaturated acids, beta unsaturated acids, such as acrylic acid, olefins, such as ethylene, butenes, and mixtures of any of these. Specific examples include ethanol, propanol, propylene glycol, butanol, 1,4-butanediol, 1,3-propanediol, methyl or ethyl esters of any of these alcohols, methyl acrylate, methylmethacrylate, Products also include sugars, e.g., glucose, xylose and xylitol. These and other products are described in U.S. Ser. No. 12/417,900 filed Apr. 3, 2009; the full disclosure of which is incorporated by reference herein.

In one aspect, the invention features a wet milling system comprising a wet mill disposed in a fluid having a biomass material dispersed therein. The system can, for example, be used for processing lingocellulosic material that has optionally been irradiated (e.g., with an electron beam). The system can include a jet mixer disposed in the fluid. The wet milling systems can include a rotor/stator head, for example with the rotor and stator including nesting rings of teeth. Furthermore, the stator can have two or more concentric rings of teeth. Other aspects of the invention include a tank with one or more jet head, and one or more wet mill disposed in the tank.

Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

All publications, patent applications, patents, and other references mentioned herein or attached hereto are incorporated by reference in their entirety for all that they contain.

DESCRIPTION OF THE DRAWINGS

FIG. 3 is a schematic diagram of an ethanol manufacturing facility that has been retrofitted to utilize the solutions and suspensions disclosed herein.

FIG. 7 is a bottom plan view of the rotor taken along view line 7-7 of FIG. 6.

FIG. 8 is a top plan view of the stator taken along view line 8-8 of FIG. 6.

DETAILED DESCRIPTION

Figure 1:
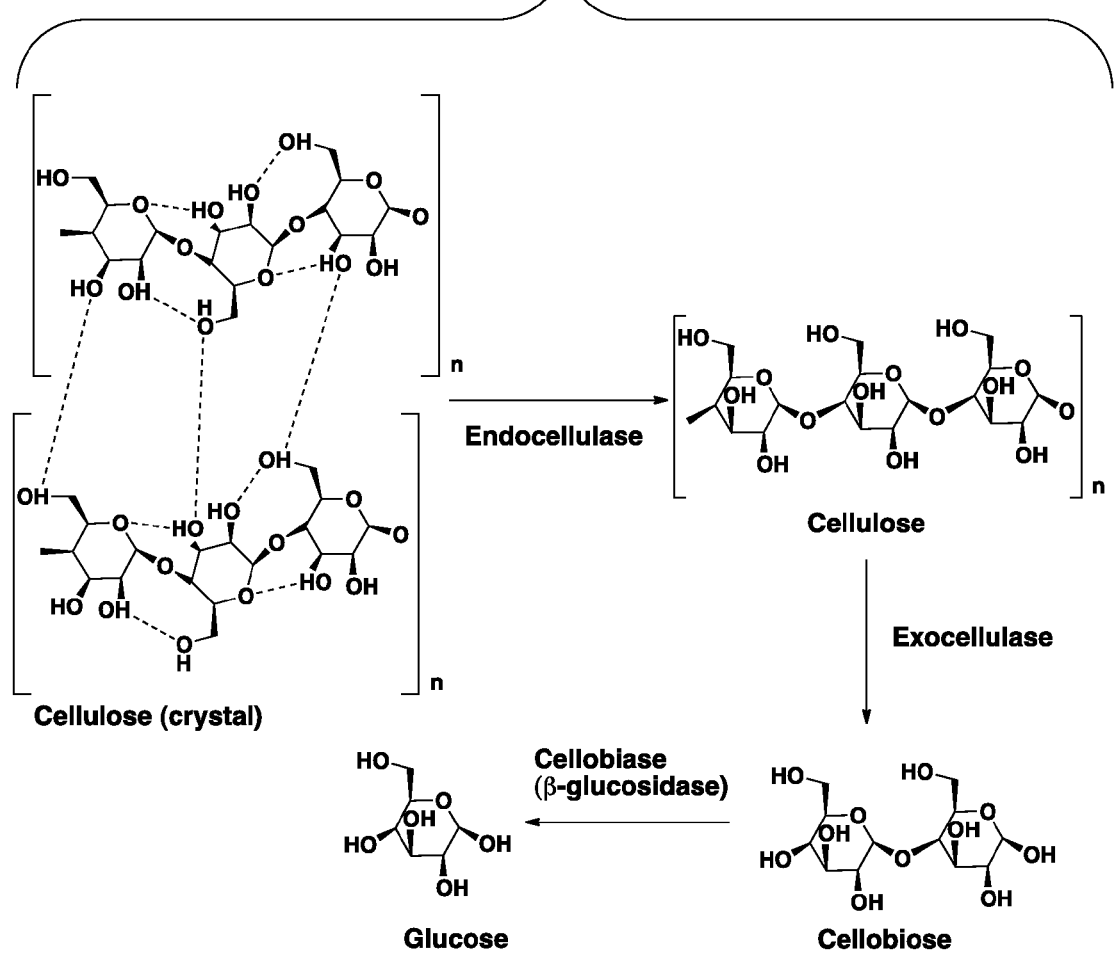
FIG. 1 is a diagram illustrating the enzymatic hydrolysis of cellulose to glucose.

Using the methods described herein, biomass (e.g., plant biomass, animal biomass, paper, and municipal waste biomass) can be processed to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

Generally, if required, materials can be physically treated for processing and/or after processing, often by size reduction. Many of the processes described herein can effectively lower the recalcitrance level of the feedstock, making it easier to process, such as by bioprocessing (e.g., with any microorganism described herein, such as a homoacetogen or a heteroacetogen, and/or any enzyme described herein), thermal processing (e.g., gasification or pyrolysis) or chemical methods (e.g., acid hydrolysis or oxidation). Biomass feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere. In some instances wet milling alone can reduce recalcitrance or act synergistically or with other treatment processes described herein.

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05. or less, e.g., less than 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 the full disclosure of which is hereby incorporated by reference.

Saccharification

In order to convert the feedstock to a form that can be readily processed, the glucan- or xylan-containing cellulose in the feedstock is hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock is combined with the saccharifying agent in a liquid medium, e.g., a solvent such as an aqueous solution, and the mixture is wet milled. Methods for wet milling the material in the liquid medium are discussed in detail below. In some implementations, during and/or after wet milling the saccharifying agent, material and liquid medium are mixed using a jet mixer. In some cases jet mixing continues throughout saccharification.

In some implementations, the material and/or the saccharifying agent are added incrementally rather than all at once. For example, a portion of the material can be added to the liquid medium, dispersed therein, and mixed with the saccharifying agent until the material is at least partially saccharified, at which point a second portion of the material is dispersed in the medium and added to the mixture. This process can continue until a desired sugar concentration is obtained.

The feedstock can be hydrolyzed using an enzyme, such as a cellulase or an amylase or mixtures of these enzymes. For example, the biomass material can be combined with the enzyme in a solvent, e.g., in an aqueous solution.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). Referring to FIG. 1, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose. Suitable cellulases will be discussed herein in a later section.

The time required for complete saccharification will depend on the process conditions and the feedstock and enzyme used. If saccharification is performed in a manufacturing plant under controlled conditions, the cellulose may be substantially entirely converted to glucose in about 12-96 hours, e.g., less than 48 hour, less than 36 hours, less than 24 hours, less than 18 hours, less than 12 hours or even less than 8 hours. If saccharification is performed partially or completely in transit, saccharification may take longer.

In some cases, saccharification is performed at a pH of about 4 to 7, e.g., about 4.5 to 6, or about 5 to 6.

It is generally preferred that the final concentration of glucose in the sugar solution be relatively high, e.g., greater than 10 wt. %, or greater than 15, 20, 30, 40, 50, 60, 70, 80, 90 or even greater than 95% by weight. This reduces the volume to be shipped, and also inhibits microbial growth in the solution. After saccharification, the volume of water can be reduced, e.g., by evaporation or distillation.

A relatively high concentration solution can be obtained by limiting the amount of medium, e.g., water, added to the feedstock with the enzyme. The concentration can be controlled, e.g., by controlling how much saccharification takes place. For example, concentration can be increased by adding more feedstock to the solution. In some cases, solids are removed during saccharification, e.g., by centrifuge, allowing more feedstock to be added. Solubility of the feedstock in the medium can be increased, for example, by increasing the temperature of the solution, and/or by adding a surfactant as will be discussed below. For example, the solution can be maintained at a temperature of 40-50° C., 50-60° C., 60-80° C., or even higher.

Fermentation

Microorganisms can produce a number of useful intermediates and products by fermenting a low molecular weight sugar produced by saccharifying the treated feedstock. For example, fermentation or other bioprocesses can produce alcohols (e.g., n-butanol, isobutanol, ethanol or erythritol), organic acids (e.g., acetic, butyric, citric or lactic acid), hydrocarbons, hydrogen, proteins or mixtures of any of these materials.

Yeast and *Zymomonas* bacteria, for example, can be used for fermentation or conversion. Other microorganisms are discussed in the Materials section, below. The optimum pH for fermentations is about pH 4 to 7. The optimum pH for yeast is from about pH 4 to 5, while the optimum pH for *Zymomonas* is from about pH 5 to 6. Typical fermentation times are about 24 to 168 (e.g., 24-96 hrs) hours with temperatures in the range of 20° C. to 40° C. (e.g., 26° C. to 40° C.), however thermophilic microorganisms prefer higher temperatures.

In some embodiments e.g., when anaerobic organisms are used, at least a portion of the fermentation is conducted in the absence of oxygen e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic conditions can be achieved or maintained by carbon dioxide production during the fermentation and no additional inert gas is needed.

In some embodiments, all or a portion of the fermentation process can be interrupted before the low molecular weight sugar is completely converted to a product (e.g. ethanol). The intermediate fermentation products include high concentrations of sugar and carbohydrates. The sugars and carbohydrates can be isolated as discussed below. These intermediate fermentation products can be used in preparation of food for human or animal consumption. Additionally or alternatively, the intermediate fermentation products can be ground to a fine particle size in a stainless-steel laboratory mill to produce a flour-like substance.

The fermentations include the methods and products that are disclosed in U.S. Provisional Application Ser. No. 61/579,559, filed Dec. 22, 2011 and U.S. Provisional Application Ser. No. 61/579,576, filed Dec. 22, 2011 the disclosure of which is incorporated herein by reference.

Mobile fermenters can be utilized, as described in U.S. Provisional Patent Application Ser. No. 60/832,735, now Published International Application No. WO 2008/011598. Similarly, the saccharification equipment can be mobile. Further, saccharification and/or fermentation may be performed in part or entirely during transit.

Fuel Cells

Where the methods described herein produce a sugar solution or suspension, this solution or suspension can subsequently be used in a fuel cell. For example, fuel cells utilizing sugars derived from cellulosic or lignocellulosic materials are disclosed in U.S. Provisional Application Ser. No. 61/579,568, filed Dec. 22, 2011, the complete disclosure of which is incorporated herein by reference.

Thermochemical Conversion

Thermochemical conversion can be performed on the treated feedstock to produce one or more desired intermediates and/or products. A thermochemical conversion process includes changing molecular structures of carbon-containing material at elevated temperatures. Specific examples include gasification, pyrolysis, reformation, partial oxidation and mixtures of these (in any order).

Gasification converts carbon-containing materials into a synthesis gas (syngas), which can include methanol, carbon monoxide, carbon dioxide and hydrogen. Many microorganisms, such as acetogens or homoacetogens are capable of utilizing a syngas from the thermochemical conversion of biomass, to produce a product that includes an alcohol, a carboxylic acid, a salt of a carboxylic acid, a carboxylic acid ester or a mixture of any of these. Gasification of biomass (e.g., cellulosic or lignocellulosic materials), can be accomplished by a variety of techniques. For example, gasification can be accomplished utilizing staged steam reformation with a fluidized-bed reactor in which the carbonaceous material is first pyrolyzed in the absence of oxygen and then the pyrolysis vapors are reformed to synthesis gas with steam providing added hydrogen and oxygen. In such a technique, process heat comes from burning char. Another technique utilizes a screw auger reactor in which moisture and oxygen are introduced at the pyrolysis stage and the process heat is generated from burning some of the gas produced in the latter stage. Another technique utilizes entrained flow reformation in which both external steam and air are introduced in a single-stage gasification reactor. In partial oxidation gasification, pure oxygen is utilized with no steam.

Systems for Treating a Feedstock

Figure 2:
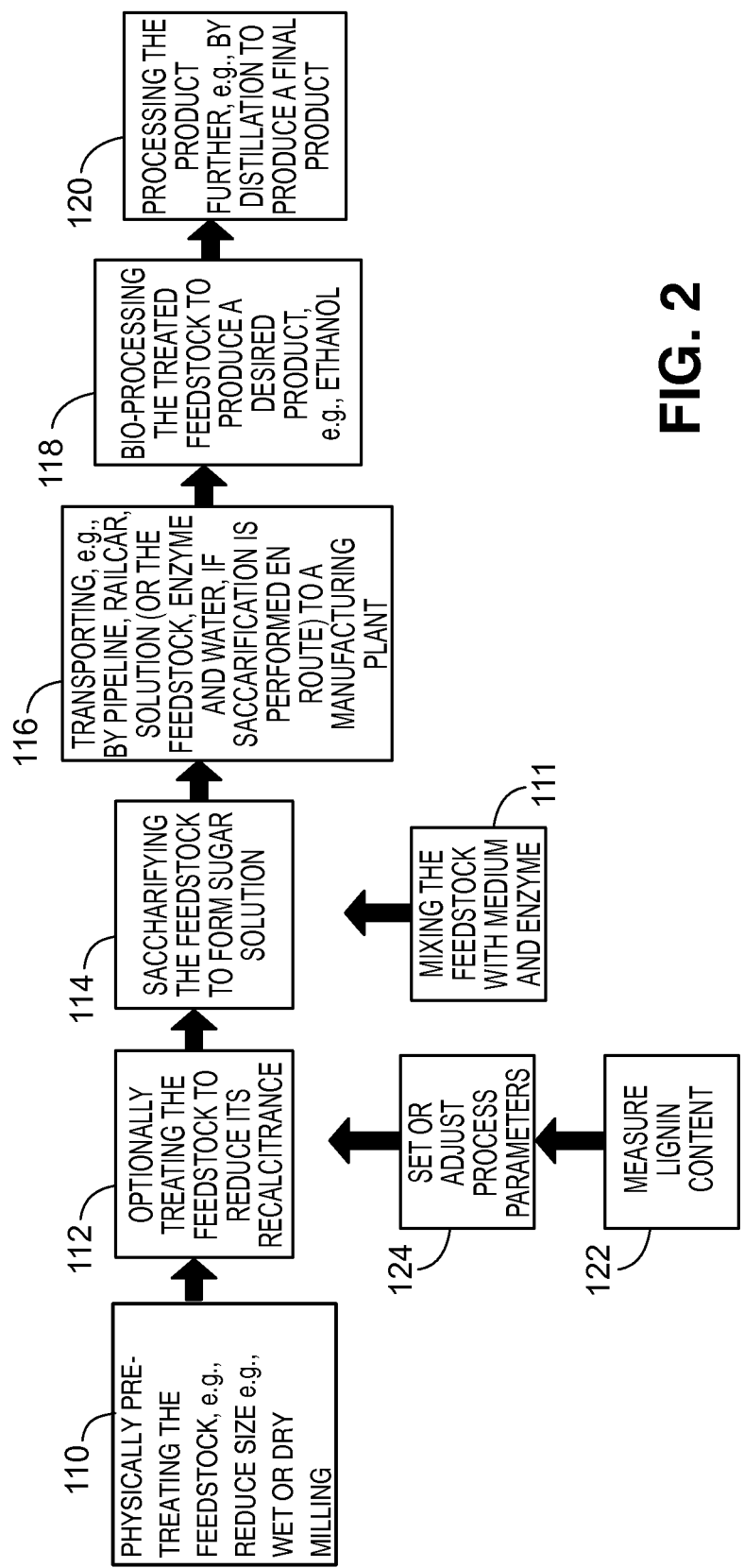
FIG. 2 is a flow diagram illustrating conversion of a feedstock to sugars and other products.

Referring to FIG. 2, a process for conversion of a feedstock to sugars and other products, e.g., ethanol, can include, for example, optionally physically pre-treating the feedstock, e.g., to reduce its size (step 110), before and/or after this treatment, optionally treating the feedstock to reduce its recalcitrance (step 112), and saccharifying the feedstock to form a sugar solution (step 114). Saccharification can be performed by mixing a dispersion of the feedstock in a liquid medium, e.g., water with an enzyme (step 111), as will be discussed in detail below. During or after saccharification, the mixture (if saccharification is to be partially or completely performed en route) or solution can be transported, e.g., by pipeline, railcar, truck or barge, to a manufacturing plant (step 116). At the plant, the solution can be bio-processed to produce a desired product, e.g., ethanol (step 118), which is then processed further, e.g., by distillation (step 120). The individual steps of this process will be described in detail below. If desired, the steps of measuring lignin content (step 122) and setting or adjusting process parameters (step 124) can be performed at various stages of the process, for example just prior to the process step(s) used to change the structure of the feedstock, as shown. If these steps are included, the process parameters are adjusted to compensate for variability in the lignin content of the feedstock, as described in U.S. application Ser. No. 12/704,519 filed in Feb. 11, 2010, the complete disclosure of which is incorporated herein by reference.

Figure 2A:
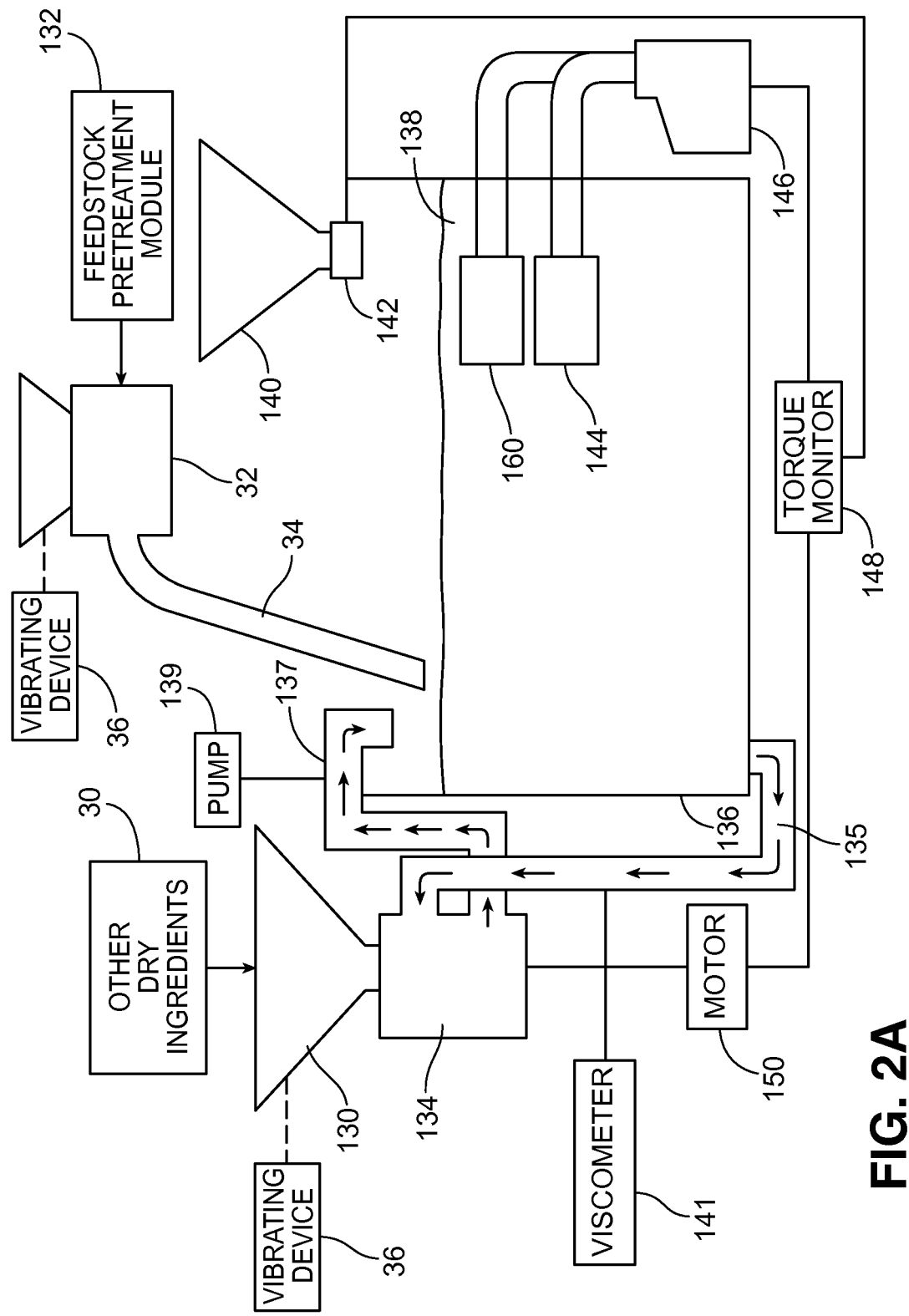
FIG. 2A is a diagrammatic illustration of a saccharification system according to one embodiment.
Figure 2B:
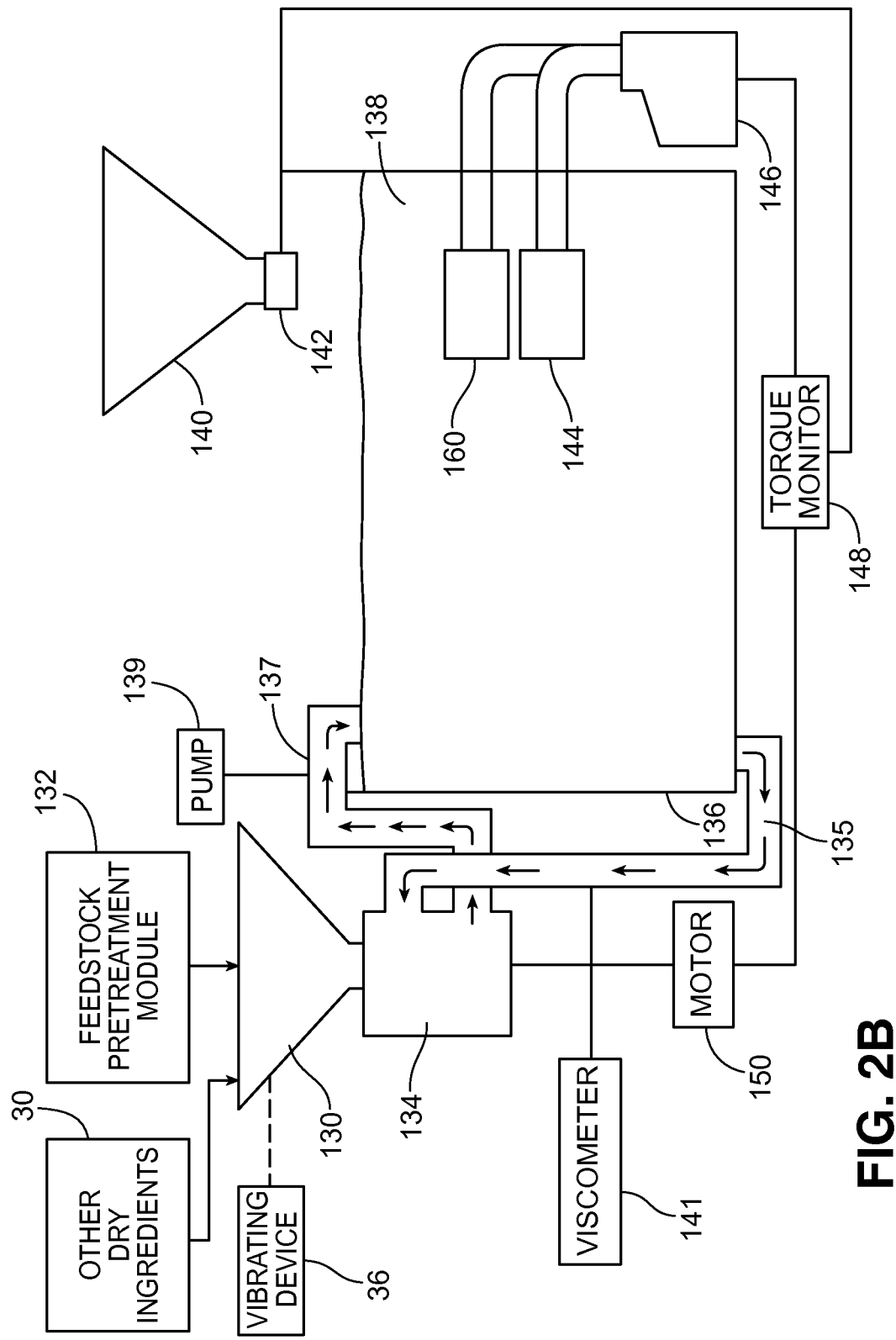
FIG. 2B is a diagrammatic illustration of a saccharification system according to another embodiment.

The mixing step 111 and saccharifying step 114 can be performed using, for example, either of the systems shown in FIGS. 2A and 2B. These systems include a tank 136, which initially contains a liquid medium and later contains a mixture 138 of liquid medium, feedstock and saccharifying agent. The liquid medium is delivered to the tank through a valved piping system (not shown). The systems also include a hopper 130, in communication with a dispersing unit 134. In the embodiment shown in FIG. 2B, the hopper 130 receives feedstock that has been treated to reduce its size and optionally to reduce its recalcitrance (steps 110 and 112 above) by a feedstock pretreatment module 132. In both embodiments, the hopper may receive other dry ingredients, such as yeast and nutrients, e.g., from a supply 30. Optionally, a vibrating device 36 may be associated with the hopper, to facilitate delivery of material from the hopper. The system may also optionally include a dispersing unit 134, e.g., if the feedstock is difficult to initially wet with the liquid. The liquid medium is drawn into the dispersing unit 134 from the tank, and returned to the tank by the dispersing unit via an outlet pipe 137. The opening of outlet pipe 137 may be above the liquid level, as shown, or may in some instances be submerged in the liquid in the tank. In some cases, depending on the type of milling unit and dispersing unit used, the system may include a pump 139, e.g., a positive displacement pump, configured to circulate the liquid medium, and/or a viscometer 141 to monitor the viscosity of the dispersion and activate the pump when the measured viscosity reaches a predetermined value.

In the embodiment shown in FIG. 2A, the feedstock is delivered to the surface of the liquid medium in the tank, e.g., via a delivery device 32 having a delivery conduit 34 (e.g., hose or pipe). The delivery device 32 may also be associated with a vibrating device 36, to facilitate flow of material into the device. The delivery device 32 may be, for example, a blower configured to blow fibrous and/or particulate material from a source to a location remote from the source through a hose, e.g., an insulation blower such as the FORCE 3 blower available from Intec, Frederick, Colo. Alternatively, the material can be delivered to the surface of the liquid using other techniques, such as gravity feed or a screw conveyor.

In some implementations, the tank is provided with a flexible, air permeable cover, or other device configured to allow air to vent from the tank during delivery of the feedstock, while preventing feedstock from blowing out of the tank and/or contaminants from entering the tank.

When the particles are generally spherical, e.g., as is the case with hammermilled corn cobs, or otherwise of a morphology that allows them to be easily fed, the feedstock can be gravimetrically fed. For example, the feedstock can be delivered from a hopper above the tank.

As the feedstock material is delivered through delivery conduit 34 onto the surface of the liquid in the tank, liquid is discharged through outlet pipe 137 of the dispersing unit 134 onto the material. The discharged liquid wets the feedstock material, causing it to sink into the liquid, where it can be dispersed by the dispersing unit 134 (if one is provided), optionally in combination with the mixing action of a jet mixer 144, discussed below.

Once the feedstock has been delivered to the tank, it is wet milled, using wet milling unit 160, which generally includes a high shear rotor/stator head. Examples of suitable milling units are described in detail below. The wet milling unit can be mounted in any desired location in the tank. It can be side-mounted, as shown, or top and bottom mounted. In some implementations, the wet milling unit can be external to the tank and the tank contents can be pumped through the wet milling unit and returned to the tank. In some cases, the wet milling unit is mounted adjacent to the jet mixing unit 144, described below. In some cases, multiple wet milling heads are provided. For example, in a large tank multiple wet milling heads may be mounted at spaced locations within the tank. Wet milling can be performed in-line or as a batch process.

Wet milling is generally performed at a high shear rate, for example from about 20,000 $sec^{-1}$ to 60,000 $sec^{-1}$, or from about 30,000 $sec^{-1}$ to 50,000 $sec^{-1}$.

The wet milling unit may be run for any desired length of time. The wet milling unit can be run in a pulsed manner (e.g., the power to the motor driving the wet milling is pulsed), for example the shearing rate can be varied periodically or non-periodically, or, as another example the wet milling unit can be turned on an off repeatedly. Generally, wet milling is discontinued when either the efficiency of saccharification ceases to be improved by wet milling (this can be determined by experimentation for a given set of process parameters), or the shear generated by the wet milling unit causes the temperature of the tank contents to exceed a predetermined maximum value. The predetermined maximum value may be set, for example, based on the temperature at which the saccharifying agent would be denatured in a short period of time.

Shearing can cause the mean particle size of the biomass material to be reduced. For example the size can be reduced from about more than 1 mm (e.g. more than 5 mm or more than 10 mm) to less than 1 mm (e.g., less than 0.5 mm, less than 0.1 mm or even less than 0.01 mm).

In some implementations, the wet milling unit can be used to heat, or partially heat, the tank contents to a desired processing temperature. For example, in one implementation the tank contents are heated by another means to approximately 40° C., and then the wet milling unit is operated for a time sufficient to raise the temperature to approximately 50° C., a temperature which is advantageous for saccharification. In some cases, wet milling is performed for less than 8 hours, e.g., for 1 to 4 hours or 1 to 2 hours. Wet milling may be performed for an even shorter time, e.g., 30 minutes or less. Once this desired temperature is reached the wet milling device is turned off so as to prevent a further increase in temperature. In some cases, the tank contents may be cooled during or after wet milling to prevent overheating. In order to prevent denaturing of the enzymes used in saccharification, it is generally preferred that the tank contents be maintained at or below 50° C., or at least that temperature excursions above 50° C. be of sufficiently short duration so as not to denature the enzymes.

Before, during, or after wet milling, a saccharifying agent is delivered to the tank from a hopper 140, which includes a metering device 142. During saccharification, the contents of the tank are mixed, e.g., by one or more jet mixers. In some cases, the jet mixers are operated during wet milling. A jet mixer 144 is represented diagrammatically in FIGS. 2A and 2B; examples of suitable jet mixers will be described in detail below, and are also described in U.S. Ser. No. 12/782,694 filed May 18, 2010; Ser. No. 13/293,985 filed Nov. 10, 2011; and Ser. No. 13/293,977 filed Nov. 10, 2011 the full disclosures of which are hereby incorporated by reference herein. The jet mixer produces a jet using a motor 146 that drives a pump and/or a rotor (not shown). The torque exerted by the motor 146 correlates with the solids level of the mixture in the tank, which in turn reflects the degree to which the mixture has saccharified. The torque is measured by a torque monitor 148, which sends a signal to a motor 150 that drives the conveyor 130 and also to the metering device 142 of the hopper 140. Thus, the supply of the treated feedstock and the enzyme can be interrupted and resumed as a function of the saccharification of the contents of the tank. The data measured by the torque monitor can also be used to adjust the jet mixer, e.g., to a lower RPM for a mixer that utilizes a rotor, or to a lower jet velocity for a pump-driven mixer. Instead of, or in addition to, the torque monitor, the system may include an Amp monitor (not shown) that measures the full load amperage of the motor. In some cases, the jet mixer may include a variable frequency drive (VFD) to allow the speed of the motor to be adjusted.

The system may also include a heat monitor (not shown) that monitors the temperature of the liquid medium and adjusts the feed rate of the feedstock and/or the mixing conditions in response to increases in temperature. Such a temperature feedback loop can be used to prevent the liquid medium from reaching a temperature that will denature the enzyme. The heat monitor can also be used to determine when to shut off the wet milling unit to avoid overheating of the tank contents.

When one or more pumps are used in the systems described herein, it is generally preferred that positive displacement (PD) pumps be used, e.g., progressive cavity or screw-type PD pumps.

In some cases, the manufacturing plant can be, for example, an existing grain-based or sugar-based ethanol plant or one that has been retrofitted by removing or decommissioning the equipment upstream from the bio-processing system (which in a typical ethanol plant generally includes grain receiving equipment, a hammermill, a slurry mixer, cooking equipment and liquefaction equipment). Thus, the feedstock received by the plant is input directly into the fermentation equipment. A retrofitted plant is shown schematically in FIG. 3. The use of an existing grain-based or sugar-based ethanol plant in this manner is described in U.S. Ser. No. 12/704,521, filed Feb. 11, 2010, the full disclosure of which is incorporated herein by reference.

In some embodiments, rather than transporting the saccharified feedstock (sugar solution) to a separate manufacturing plant, or even a separate tank, the sugar solution is inoculated and fermented in the same tank or other vessel used for saccharification. Fermentation can be completed in the same vessel, or can be started in this manner and then completed during transport as discussed above. Saccharifying and fermenting in a single tank are described in U.S. application Ser. No. 12/949,044, Nov. 18, 2011, the full disclosure of which is incorporated herein by reference.

Generally, the oxygen level in the fermentation vessel should be controlled, e.g., by monitoring the oxygen level and venting the tank, aerating (e.g., by mixing or sparging in oxygen or mixtures of gases containing oxygen) or de-aerating (e.g., by mixing in or sparging in inert gases such as nitrogen, carbon dioxide, helium and/or argon) the mixture as necessary. In some cases, for example where anaerobic conditions are desirable as discussed previously, the rate of mixing is critical. For example, at times during the process, no mixing may be desirable so that gases produced during fermentation (e.g., $CO_2$, $H_2$ and or methane) can more effectively displace oxygen from the fermentation vessel. It is also desirable to monitor the level of ethanol in the vessel, so that when the ethanol level begins to drop the fermentation process can be stopped, e.g., by heating or the addition of sodium bisulfite. Other methods of stopping fermentation include adding a peroxide (e.g., peroxy acetic acid or hydrogen peroxide), adding succinic acid or a salt thereof, cooling the contents of the vessel, or reducing the oxygen sparge rate. Combinations of any two or more of these methods may be used. If fermentation is to be conducted or completed during transport, the transportation vessel (e.g., the tank of a rail car or tanker truck) can be fitted with a control unit that includes an oxygen monitor and ethanol monitor, and a delivery system for delivering sodium bisulfite (or other fermentation terminating additive) to the tank and/or a system for adjusting the parameters in the tank to stop fermentation.

If desired, jet mixing can be utilized during fermentation, and if fermentation is conducted in the same vessel as saccharification the same jet mixing equipment can be utilized. However, in some embodiments jet mixing is not necessary. For example, if fermentation is conducted during transport the movement of the rail car or tanker truck may provide adequate agitation.

Dispersing, Wet Milling, and Mixing

Systems are disclosed herein that include one or more tanks, one or more agitators, e.g., one or more jet head agitators, and one or more wet mills. In some instances, all mills and agitator heads are within tanks.

Dispersing

The optional dispersing unit 134 may include any type of dispersing equipment that wets the feedstock with the liquid medium. Many dispersing units include a chamber and a rotor in the chamber positioned such that the feedstock and liquid medium are drawn towards the rotor axially, and forced outward radially to the periphery of the rotor and thus through the outlet of the unit, in the manner of a centrifugal pump. Depending upon the construction of the dispersing unit, a back-up pump may be required (pump 139, discussed above) to draw the fluid through the dispersing unit at high viscosities. Some dispersing units are constructed to generate very high static fluid pressure within the unit; when such units are used a back-up pump is generally not required.

Example of suitable dispersing systems are disclosed in U.S. Ser. No. 12/949,004, filed Nov. 18, 2010, the full disclosure of which is incorporated herein by reference.

Wet Milling

Two examples of wet milling heads for use in wet milling unit 160 are shown in FIGS. 4-10 and FIGS. 11-17. Each head includes a rotor and a stator, and is mounted on a shaft (not shown) as is well known in the rotor/stator mixer art. In both cases, when the rotor and stator are assembled, the gaps between the teeth of the rotor are out of alignment with the gaps between the teeth of the stator. This creates a shearing gap through which liquid flows under high shear during rotation of the rotor.

Wet milling devices are commercially available, for example, from Quadro Engineering, (Waterloo Ontario), IKA Works Inc., (Wilmington, Del.), Admix Inc. (Manchester, N.H.) and Silverson, (Dartmouth Mass.).

Figure 5:
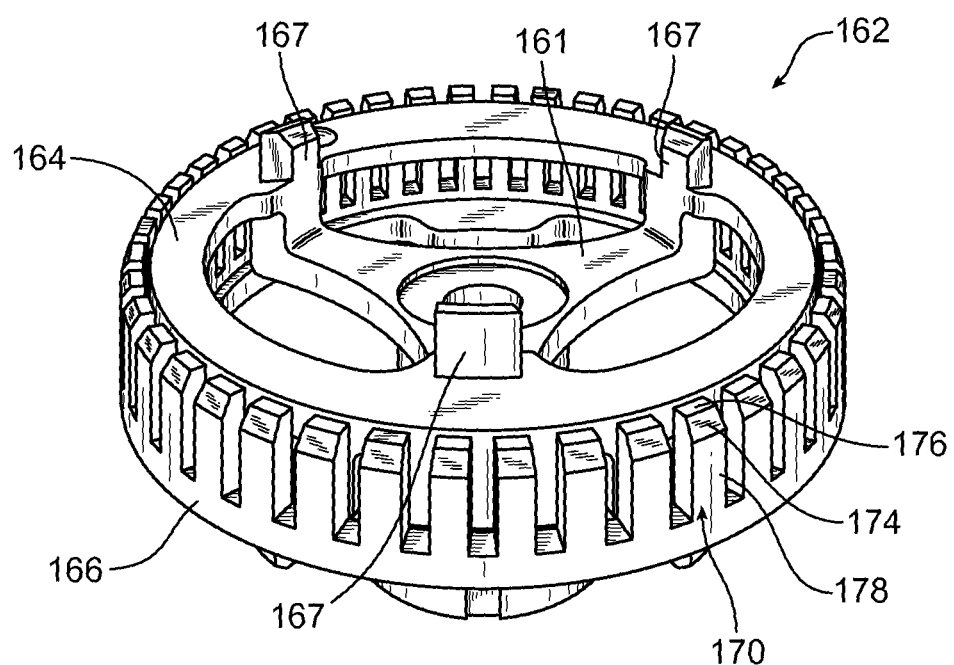
FIG. 5 is a perspective view of the rotor and stator together.
Figure 6:
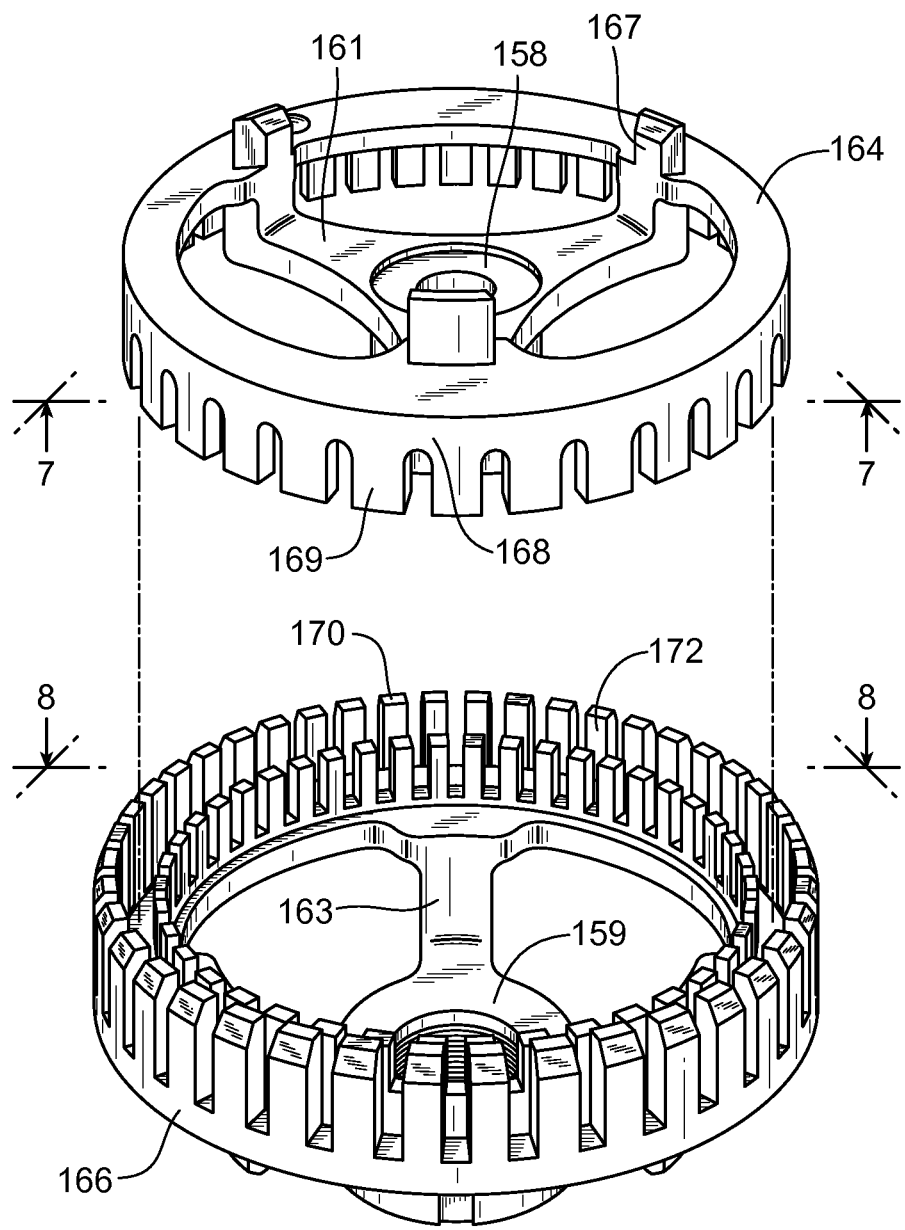
FIG. 6 is an exploded perspective of the rotor and stator.

In the implementation shown in FIGS. 4-10, the stator includes two concentric rings of teeth (see FIG. 6). Under a given set of conditions, this stator configuration will generally produce higher shear than the single ring stator configuration shown in FIGS. 11-17. On the other hand, the rotor of the head shown in FIGS. 11-17 includes an impeller-like portion, as will be shown below, which provides a pumping action which may be desirable in certain cases.

Referring to FIGS. 4-10, head 162 includes a rotor 164 and a stator 166. The rotor and stator each include a central hub 158 and 159, respectively, which define apertures dimensioned to receive a shaft (not shown). The shaft is connected to a motor for rotation of the rotor within the stator, with the aperture in the rotor being keyed with the shaft and the shaft rotating freely within the aperture in the stator as is well known in the art.

Arms 161 and 163, respectively, extend from the hubs to support rotor and stator toothed rings. As shown in FIGS. 6 and 8, the stator 166 includes two rings of teeth—an outer ring of teeth 170 and an inner ring of teeth 171. The rotor 164 includes a single ring of teeth 169, which fit between the rings of the stator in a nested relationship. The upper surface 165 of rotor 164 includes three projections 167 which create turbulence around the head.

Figure 4:
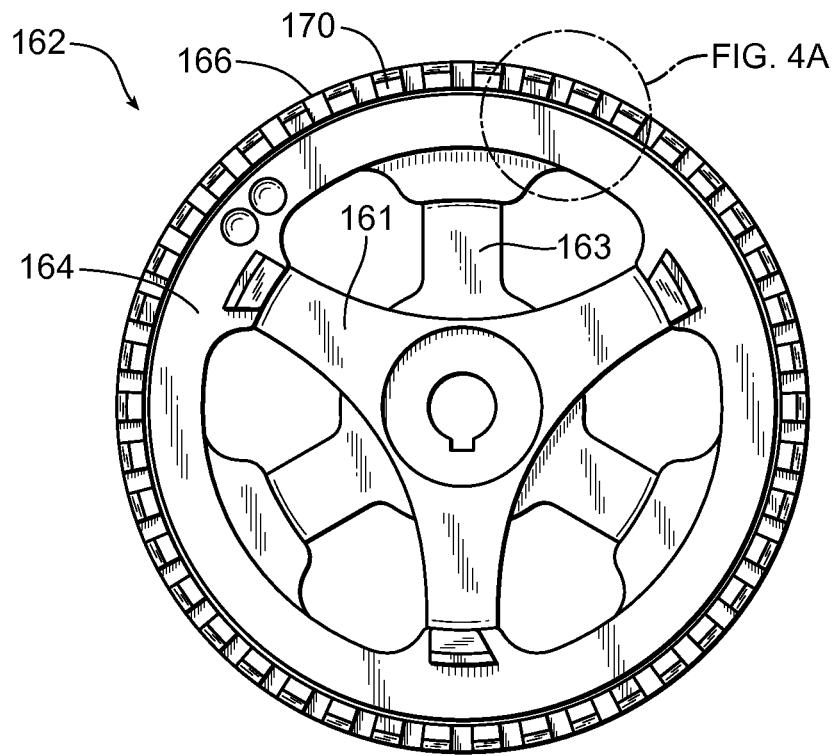
FIG. 4 is a top plan view of the assembled rotor and stator of a wet milling head according to one embodiment.
Figure 4A:
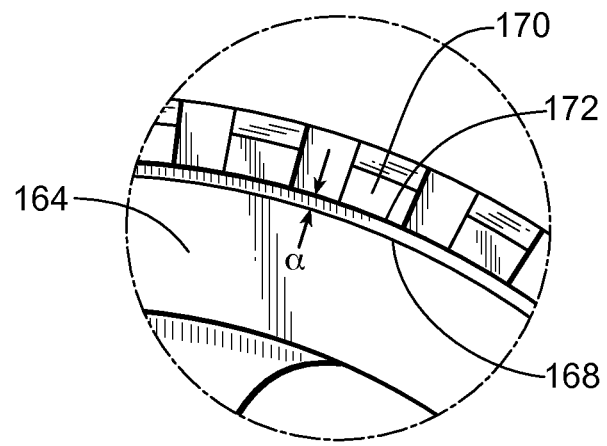
FIG. 4A is an enlarged section view of FIG. 4 showing the clearance between the rotor and stator.

As shown in FIG. 4A, a clearance α is provided between the outer surface 168 of the teeth 169 of the rotor (the OD of the rotor) and the adjacent inner surface 172 of the outer ring of teeth 170 of the stator. Clearance α is preferably small, to generate high shear, and may be, for example, from about 0.01 to 0.250 inch (0.25 to 0.64 mm), e.g., from about 0.03 to 0.10 inch (0.76 to 2.5 mm). The distance between the inner and outer rings of the stator is equal to this clearance plus the radial thickness of the teeth of the rotor, discussed below.

The outer diameters of the rotor and stator (OD1 and OD2, FIGS. 7 and 8) will depend on the volume of the tank in which the milling head is used, and how many milling heads are positioned in the tank. The outer diameter of the stator, OD2, can be, for example, from about 3 to 50", e.g., from about 5 to 25 inches, with larger heads being used in larger tanks. As an example, a 4" stator may be used in a 300 gallon tank.

As shown in FIG. 5, each tooth 170 on the outer ring of the stator includes a chamfer 174 between its top surface 176 and outer side wall 178.

Figure 9:
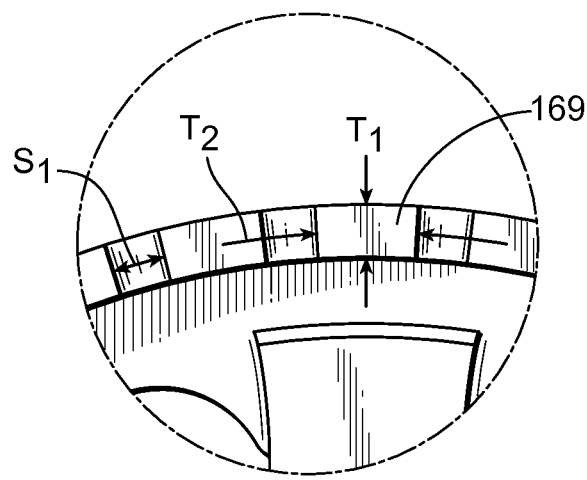
FIG. 9 is an enlarged view of the area of the rotor indicated in FIG. 7.
Figure 10:
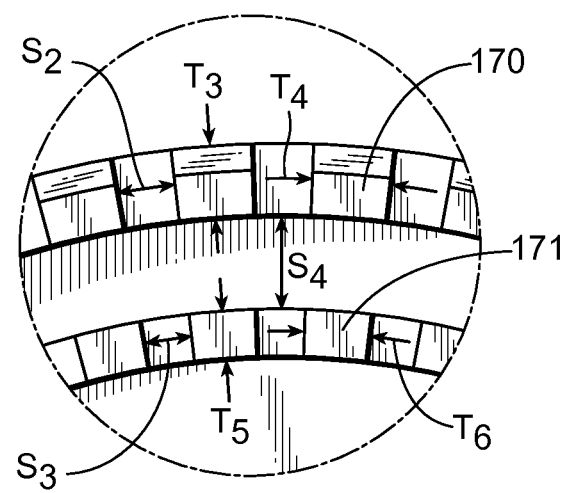
FIG. 10 is an enlarged view of the area of the stator indicated in FIG. 8.

The circumferential spacing between adjacent teeth is generally the same for the rotor (S1, FIG. 9) and both rings of the stator (S2 and S3, FIG. 10). Like the clearance α, this spacing will also affect the amount of shear generated by the head during rotation of the stator, with a larger spacing resulting in reduced shear. In some implementations, the spacing S1, S2 and S3 is about 0.1 to 0.5 inch (2.5 to 12.5 mm).

The tooth size may vary to some extent based on the desired head diameter, with larger heads having in some cases somewhat larger teeth for durability. However, generally the tooth size and tooth spacing will remain relatively constant as head diameter increases, with the number of teeth increasing with increasing head diameter. Referring to FIGS. 9 and 10, in some implementations the tooth dimensions can be, for example, as follows:

T1: 0.10"
T2: 0.35"
T3: 0.10"
T4: 0.30"
T5: 0.10"
T6: 0.30"

where T1 is the radial thickness of the rotor teeth, T2 is the circumferential thickness of the rotor teeth, T3 is the radial thickness of the outer stator teeth, T4 is the circumferential thickness of the outer stator teeth, and T5 and T6 are, respectively, the radial and circumferential thicknesses of the inner stator teeth.

As noted above, an alternative embodiment is shown in FIGS. 11-17, in which the stator has only a single row of teeth. This embodiment also differs from that shown in FIGS. 4-10 in other respects.

Figure 11:
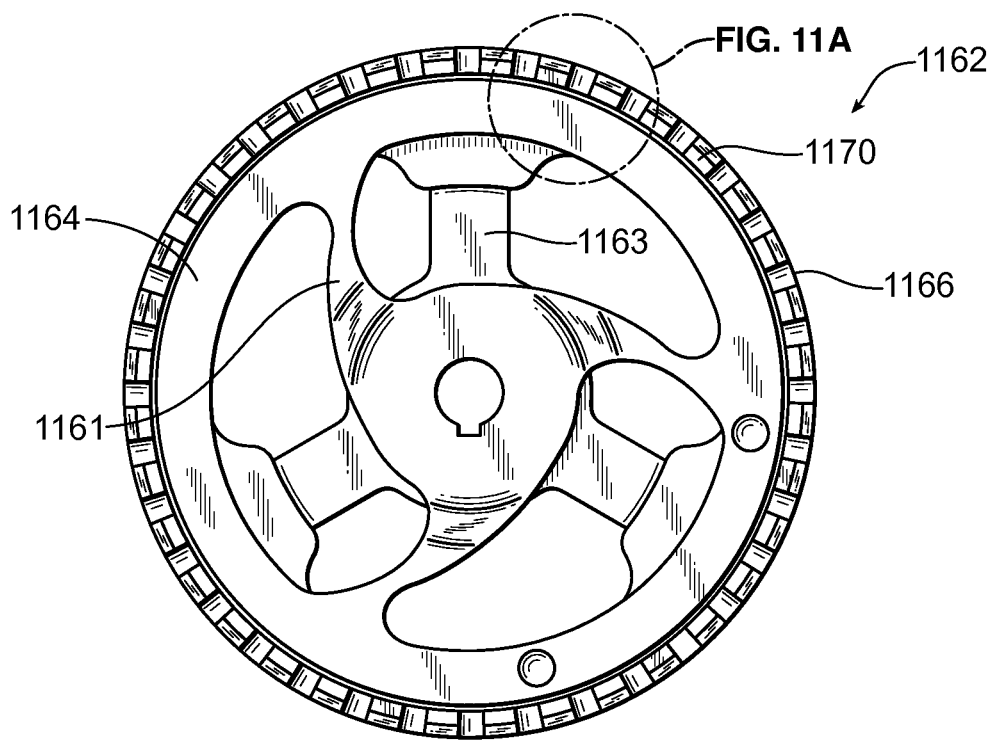
FIG. 11 is a top plan view of the assembled rotor and stator of a wet milling head according to a second embodiment.
Figure 11A:
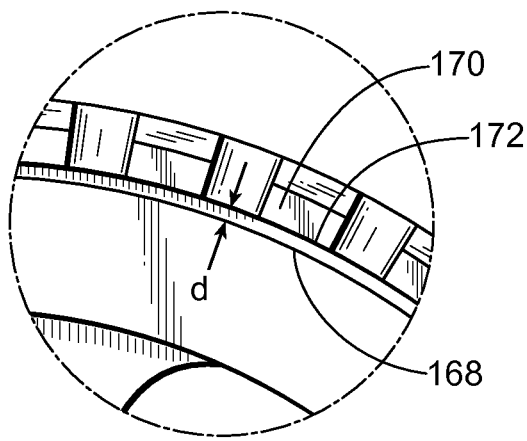
FIG. 11A is an enlarged section view of FIG. 11 showing the clearance between the rotor and stator.
Figure 12:
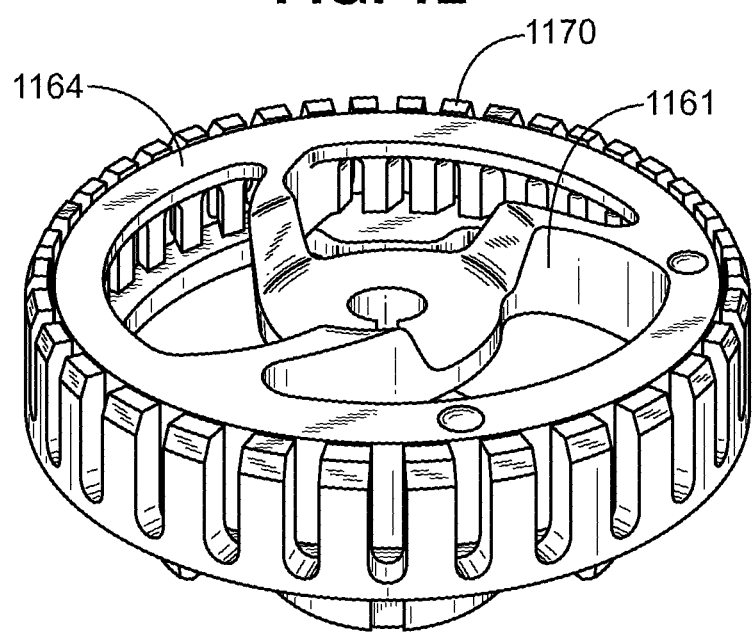
FIG. 12 is a perspective view of the rotor and stator together.
Figure 13:
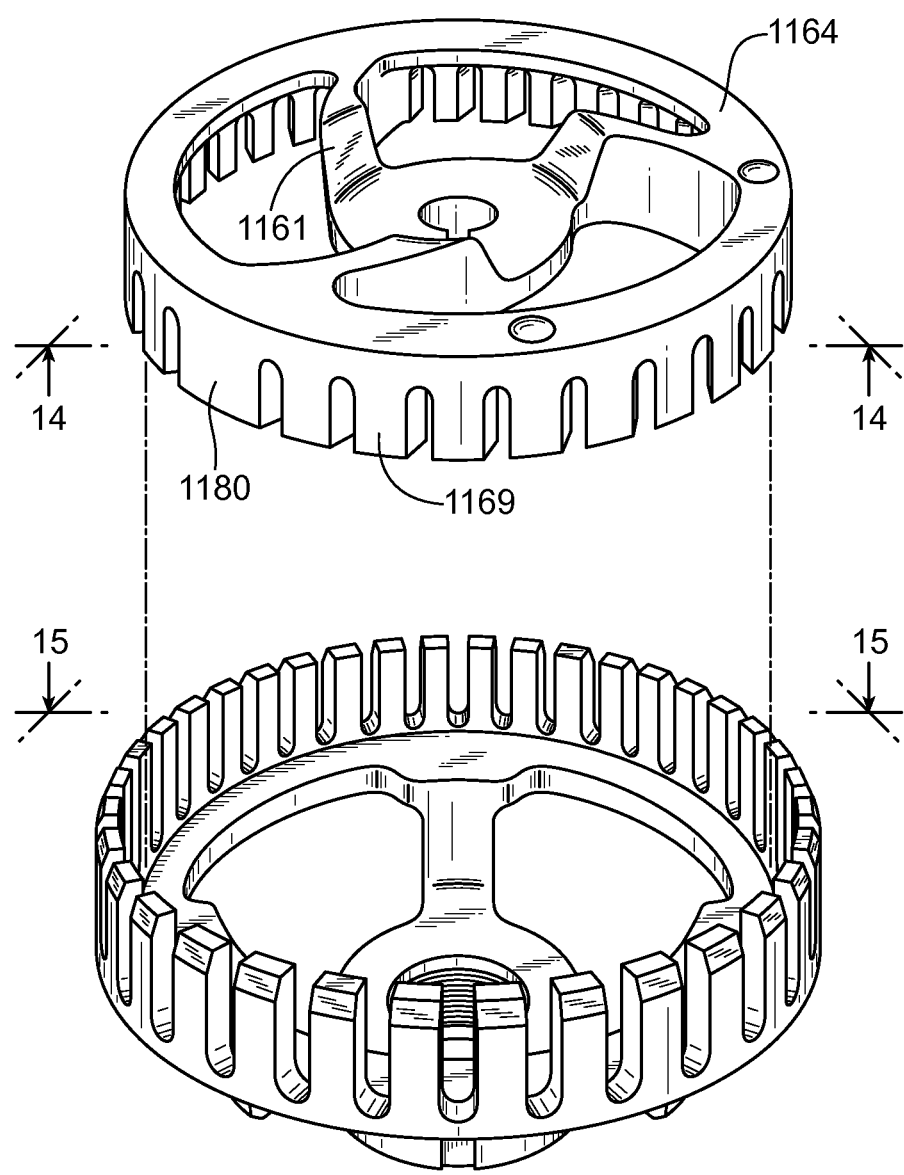
FIG. 13 is an exploded perspective of the rotor and stator.

First, the arms 1161 of the rotor are curved in two planes, as shown in FIGS. 11-13, causing the rotor to act as an impeller in addition to its shearing action in the rotor/stator arrangement. This impeller functionality is enhanced by the presence of three larger teeth 1180 (see FIGS. 13 and 14) in the rotor ring, which act as extensions of the rotor arms.

Figure 14:
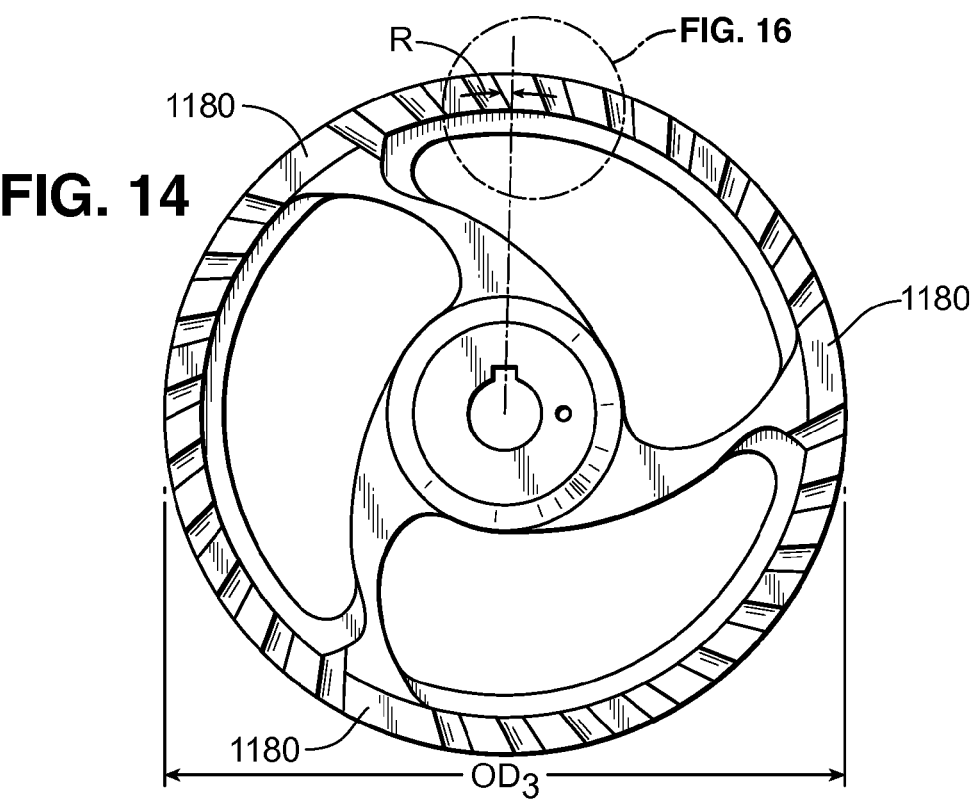
FIG. 14 is a bottom plan view of the rotor taken along view line 14-14 of FIG. 13.
Figure 15:
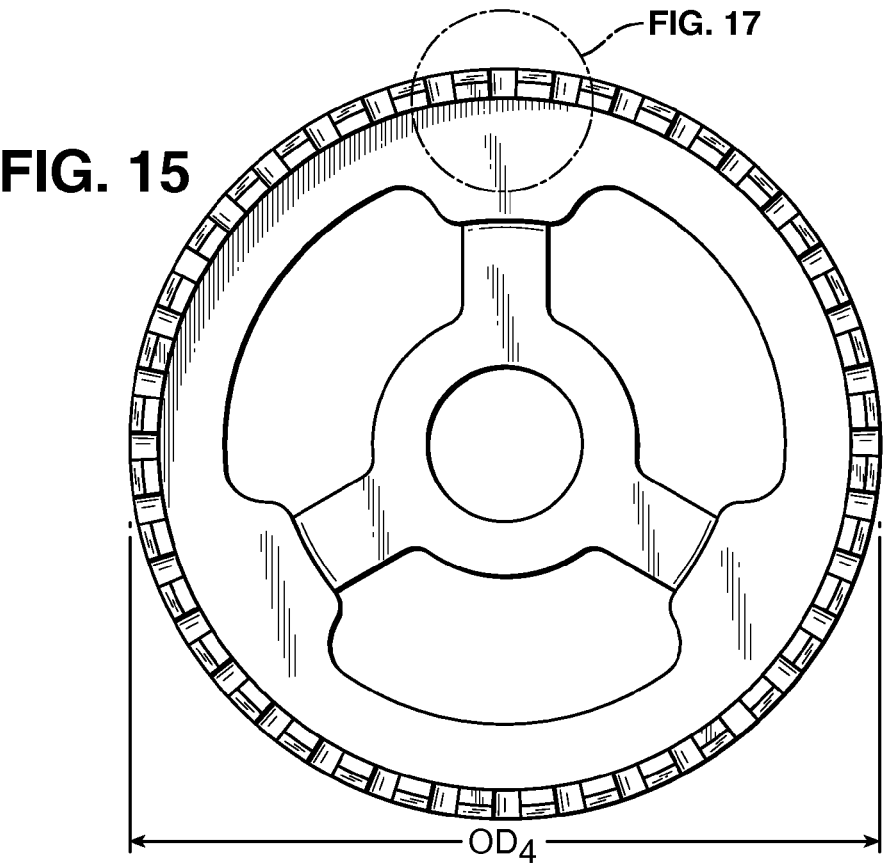
FIG. 15 is a top plan view of the stator taken along view line 15-15 of FIG. 13.
Figure 16:
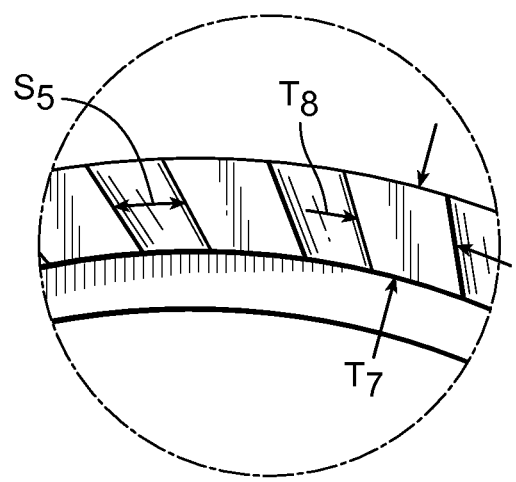
FIG. 16 is an enlarged view of the area of the rotor indicated in FIG. 14.
Figure 17:
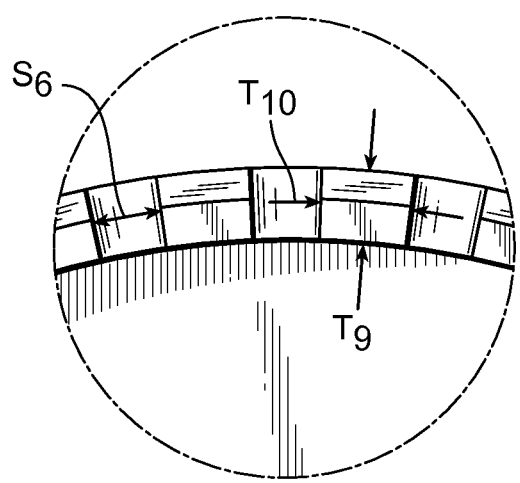
FIG. 17 is an enlarged view of the area of the stator indicated in FIG. 15.

Second, the adjacent side walls 1182 of the teeth 1169 of the rotor are not arranged at an angle R with respect to the radii of the ring, as best seen in FIGS. 14 and 16. This angle may be, for example, from about 0 to 30 degrees. The angle of the teeth helps to pump material through the gap.

The dimensions of the rotor and stator in this embodiment are generally the same as those described above for the embodiment shown in FIGS. 11-17.

The rotor or stator can be made with a variety of materials. For example, ceramics (e.g., oxides, carbides or nitrides), stainless steel, or super alloys (e.g., Hastelloy, Inconel, Waspaloy, Ren alloys, Haynes alloys, TMS alloys and CMSX single crystal alloys).

The rotor/stator head is in some cases interchangeable with the jet mixing heads described below, in particular those shown in FIGS. 19-19B. For example, in the case of converting a jet mixer to a rotor/stator, shroud 208 (FIG. 19) and mixing element 206 (FIG. 19A) are removed and the rotor/stator head is mounted on shaft 204.

Figure 20:
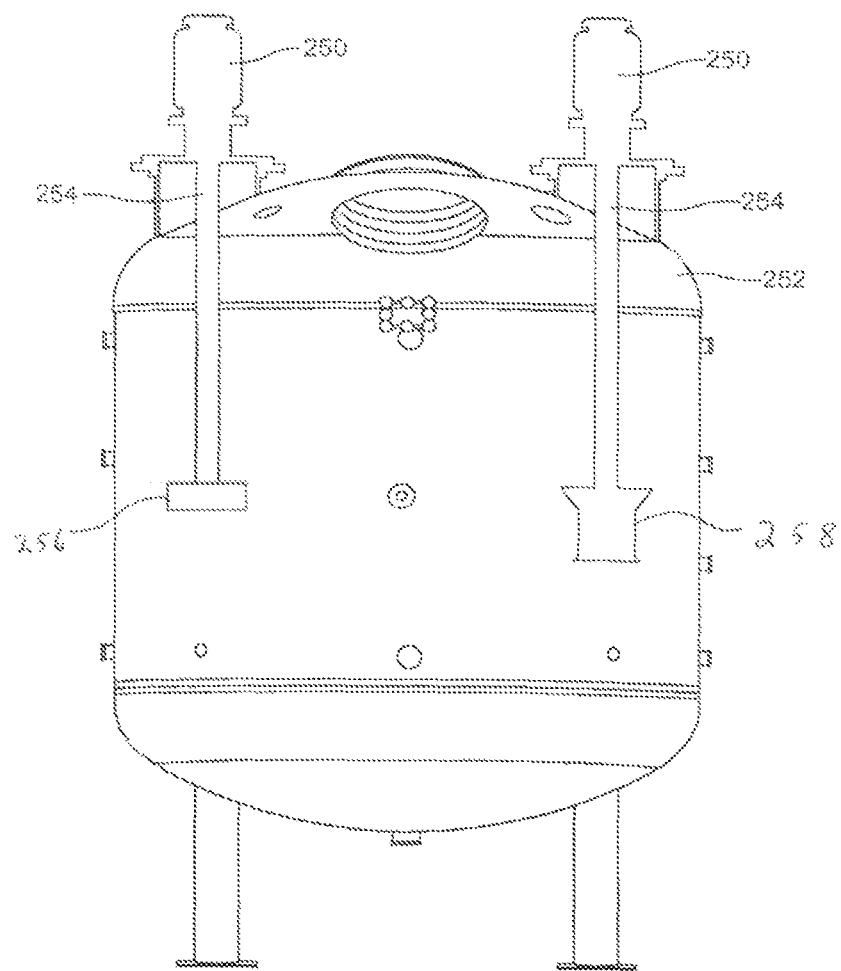
FIG. 20 is a cross-sectional view of a system for wet milling.

FIG. 20 shows a cross-sectional view of a system for wet milling that includes a tank (252), two motors (250) two shafts (254), a wet milling head (256) and a jet mixer head (258). As shown, one of the shafts is connected to one of the motors on one end and a wet milling head, as described above. Also as shown, the other shaft is connected to the other motor on one end and a jet milling head on the other end.

Jet Mixing

Particularly advantageous mixers for use during saccharification and fermentation are known as "jet mixers." In general, suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the saccharifying agent (or microorganism, e.g., in the case of fermentation). As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the tank, depending on the orientation of the mixing element. Mixing elements can be positioned in different orientations to disperse both floating and settling material, and the orientation of the mixing elements can in some cases be adjustable.

In some preferred mixing systems the velocity $v_o$ of the jet as meets the ambient fluid is from about 2 to 300 m/s, e.g., about 5 to 150 m/s or about 10 to 100 m/s. The power consumption of the mixing system may be about 20 to 1000 KW, e.g., 30 to 570 KW, 50 to 500 KW, or 150 to 250 KW for a 100,000 L tank.

Jet mixing involves the discharge of a submerged jet, or a number of submerged jets, of high velocity liquid into a fluid medium, in this case the mixture of biomass feedstock, liquid medium and saccharifying agent. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle. The longer the flow continues before it hits any obstacle, the more liquid is entrained into the secondary flow, increasing the bulk flow in the tank or vessel. When it encounters an obstacle, the secondary flow will lose momentum, more or less depending on the geometry of the tank, e.g., the angle at which the flow impinges on the obstacle. It is generally desirable to orient the jets and/or design the tank so that hydraulic losses to the tank walls are minimized. For example, it may be desirable for the tank to have an arcuate bottom (e.g., a domed headplate), and for the jet mixers to be oriented relatively close to the sidewalls. The tank bottom (lower head plate) may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the tank, creating high-velocity jets that entrain other fluid. The result is shear (fluid against fluid) and circulation, which mix the tank contents efficiently.

Figure 18:
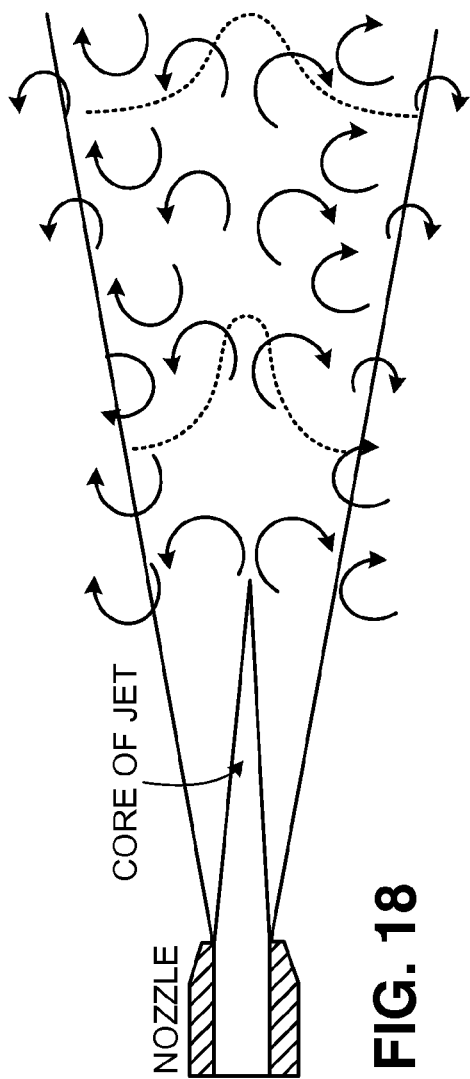
FIGS. 18 and 18A are diagrams illustrating jet flow exiting a jet mixer nozzle.
Figure 18A:
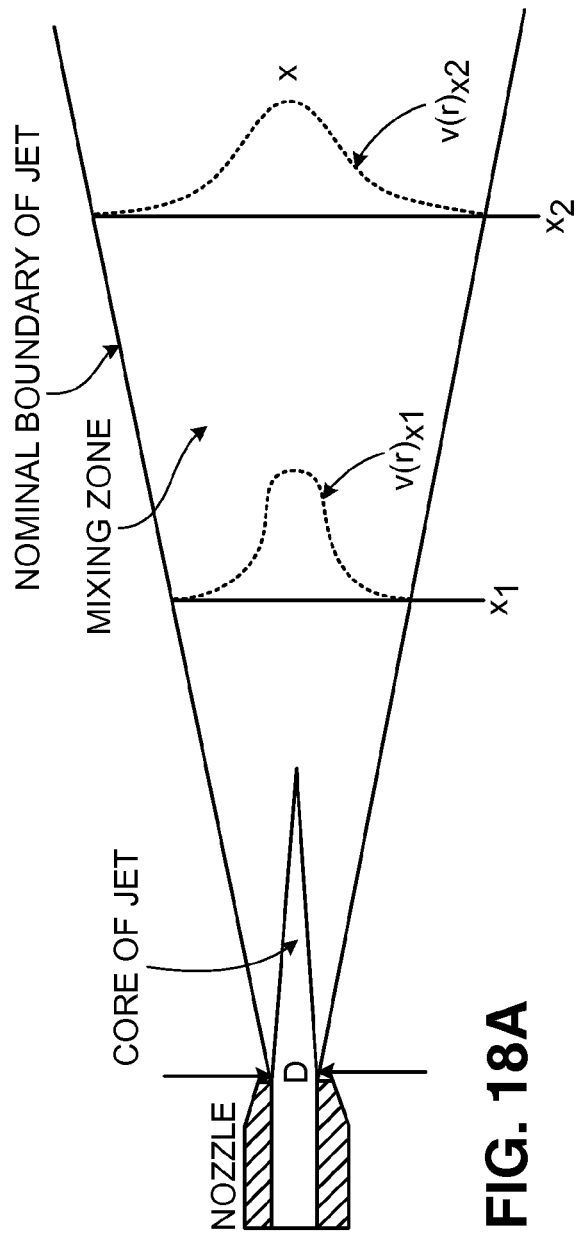

Referring to FIG. 18, the high velocity gradient between the core flow from a submerged jet and the surrounding fluid causes eddies. FIG. 18A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for $v(x)_{r=0}/v_o$ (centerline velocity), $v(r)_x/v(x)_{r=0}$ (velocity profile at a given x), $Q_x/Q_o$ (flow entrainment), and $E_x/E_o$ (energy change with x):

(1) Centerline velocity, $v(x)_{r=0}/v_o$:

$$\frac{v(r=0)}{v_o}\frac{x}{D_o} = 6.2$$

(2) velocity profile at any x, $v(r)_x/v(x)_{r=0}$:

$$\log\left[\frac{v(r)_x}{v_o}\frac{x}{D}\right] = 0.79 - 33\frac{r^2}{x^2}$$

(3) Flow and energy at any x:

$$\frac{Q_x}{Q_o} = 0.32\frac{x}{D_o} \quad (10.21)$$

$$\frac{E_x}{E_o} = 4.1\frac{D_o}{x} \quad (10.22)$$

where:
v(r=0)=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (me/s),
$Q_o$=flow of fluid emerging from the nozzle (m3/s),
E=energy flux of fluid across any given plane at distance x from the nozzle (m³/s),
$E_o$=energy flux of fluid emerging from the nozzle (m³/s).
("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measurable extent.

Jet-Flow Agitators

Figure 19:
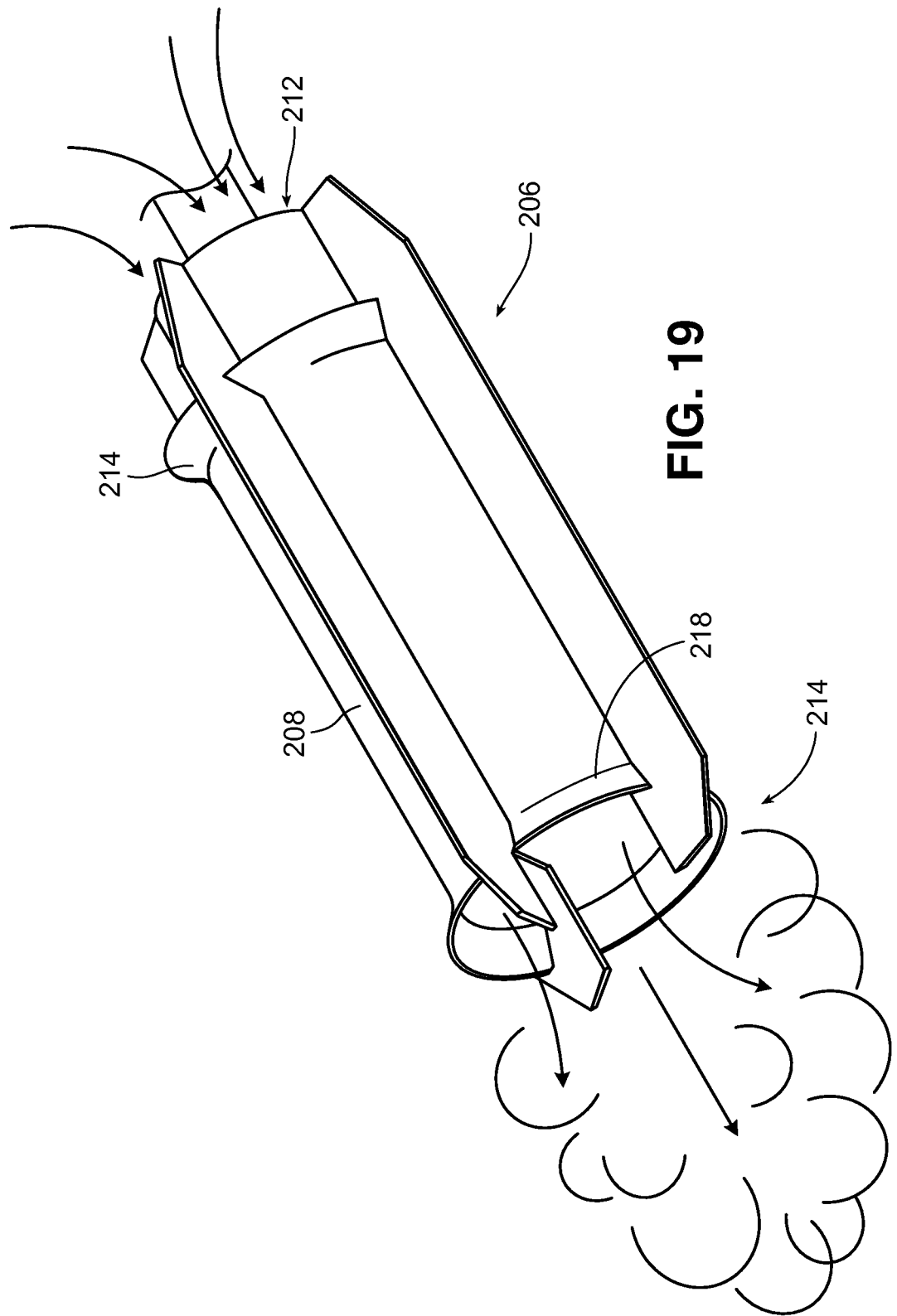
FIG. 19 is a diagrammatic perspective view of a jet-flow agitator according to one embodiment.
Figure 19A:
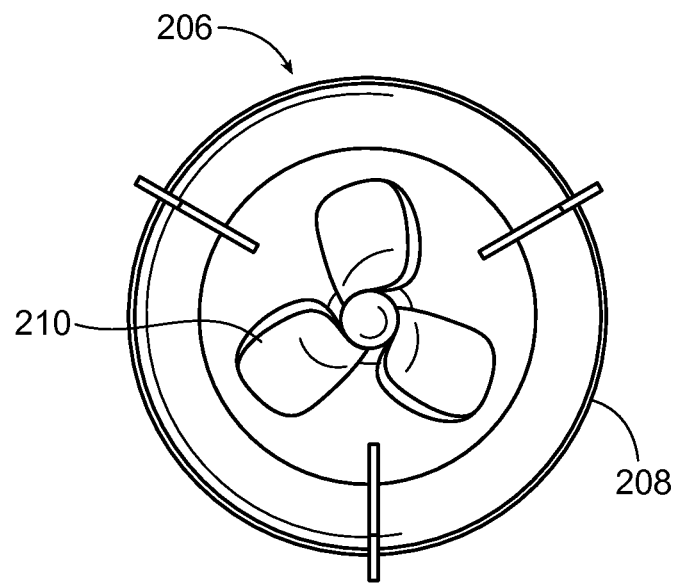
FIG. 19A is an enlarged perspective view of the impeller and jet tube of the jet-flow agitator of FIG. 19.
Figure 19B:
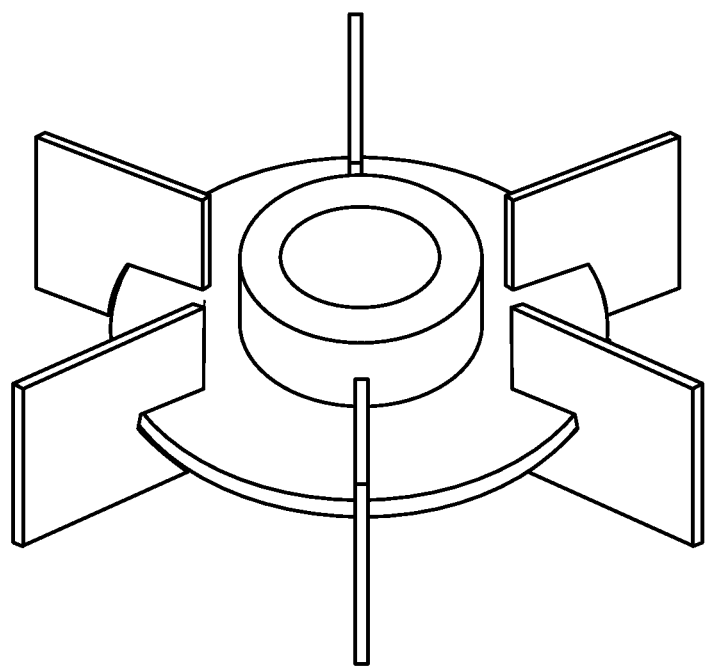
FIG. 19B is an enlarged perspective view of an alternate impeller.

One type of jet-flow agitator is shown in FIGS. 19-19A. This type of mixer is available commercially, e.g., from IKA under the tradename ROTOTRON™. Referring to FIG. 19, the mixer 200 includes a motor 202, which rotates a drive shaft 204. A mixing element 206 is mounted at the end of the drive shaft 204. As shown in FIG. 19A, the mixing element 206 includes a shroud 208 and, within the shroud, an impeller 210. As indicated by the arrows, when the impeller is rotated in its "forward" direction, the impeller 210 draws liquid in through the open upper end 212 of the shroud and forces the liquid out through the open lower end 214. Liquid exiting end 214 is in the form of a high velocity stream or jet. If the direction of rotation of the impeller 210 is reversed, liquid can be drawn in through the lower end 214 and ejected through the upper end 212. This can be used, for example, to suck in solids that are floating near or on the surface of the liquid in a tank or vessel. (It is noted that "upper" and "lower" refer to the orientation of the mixer in FIG. 19; the mixer may be oriented in a tank so that the upper end is below the lower end.)

The shroud 208 includes flared areas 216 and 218 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 208 and the impeller 210 is sufficient so as to avoid excessive milling of the material as it passes through the shroud. For example, the clearance may be at least 10 times the average particle size of the solids in the mixture, preferably at least 100 times.

In some implementations, the shaft 204 is configured to allow gas delivery through the shaft. For example, the shaft 204 may include a bore (not shown) through which gas is delivered, and one or more orifices through which gas exits into the mixture. The orifices may be within the shroud 208, to enhance mixing, and/or at other locations along the length of the shaft 204.

The impeller 210 may have any desired geometry that will draw liquid through the shroud at a high velocity. The impeller is preferably a marine impeller, as shown in FIG. 19A, but may have a different design, for example, a Rushton impeller as shown in FIG. 19B, or a modified Rushton impeller, e.g., tilted so as to provide some axial flow.

In order to generate the high velocity flow through the shroud, the motor 202 is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. For example, a mixer sized to mix a 10,000-20,000 liter tank may operate at speeds of 900 to 1,200 RPM. The torque of the motor is preferably self-adjusting, to maintain a relatively constant impeller speed as the mixing conditions change over time, e.g., due to saccharification of the solids.

Advantageously, the mixer can be oriented at any desired angle or location in the tank, to direct the jet flow in a desired direction. Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode during initial dispersion of the feedstock in the liquid medium, particularly if the feedstock is dumped or blown onto the surface of the liquid, as up pumping creates significant turbulence at the surface. Up pumping can also be used during fermentation to help remove $CO_2$ from the liquid by causing the gas to bubble to the surface where it can be vented.

Other suitable jet mixers are described in U.S. application Ser. No. 12/782,694 filed May 18, 2011; Ser. No. 13/293,985 filed Nov. 10, 2011; Ser. No. 13/293,977 filed Nov. 10, 2011 and U.S. Ser. No. 12/782,694, filed May 18, 2010, the full disclosures of which are incorporated herein by reference.

Materials

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, switchgrass, alfalfa, hay, corn cobs, corn stover, wheat straw, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307; 6,258,876; 6,207,729; 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

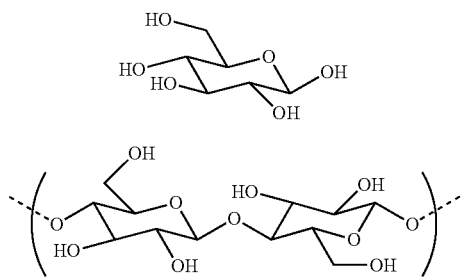

In some embodiments, the biomass material includes starchy materials, e.g., corn starch, wheat starch, potato starch or rice starch, a derivative of starch, or a material that includes starch, such as an edible food product or a crop. For example, the starchy material can be arracacha, buckwheat, banana, barley, corn kernels, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plan, a part of a plant or different parts of a plant e.g., a wheat plant, cotton plant, a corn plant, rice plant or a tree. The starchy materials can be treated by any of the methods described herein.

In other embodiments, the biomass materials, such as cellulosic, starchy and lignocellulosic feedstock materials, can be obtained from plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogeneous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Ser. No. 13/396,369 filed Feb. 14, 2012 the full disclosure of which is incorporated herein by reference.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Saccharifying Agents

Suitable enzymes include cellobiases, cellulases and amylases capable of degrading biomass.

Suitable cellobiases include a cellobiase from *Aspergillus niger* sold under the tradename NOVOZYME 188™.

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS 117.65, Cephalosporium sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencore under the tradename ACCELLERASE®, for example, Accellerase® 1500 enzyme complex. Accellerase® 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

In some implementations, the saccharifying agent comprises an acid, e.g., a mineral acid. When an acid is used, co-products may be generated that are toxic to microorganisms, in which case the process can further include removing such co-products. Removal may be performed using an activated carbon, e.g., activated charcoal, or other suitable techniques.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212). Other suitable microorganisms include, for example, *Zymomonas mobilis, Clostridium thermocellum* (Philippidis, 1996, supra), *Clostridium saccharobutylacetonicum, Clostridium saccharobutylicum, Clostridium Puniceum, Clostridium beijernckii, Clostridium acetobutylicum, Moniliella pollinis, Yarrowia lipolytica, Aureobasidium* sp., *Trichosporonoides* sp., *Trigonopsis variabilis, Trichosporon* sp., *Moniliellaacetoabutans, Typhula variabilis, Candida magnoliae, Ustilaginomycetes, Pseudozyma tsukubaensis*, yeast species of genera *Zygosaccharomyces, Debaryomyces, Hansenula* and *Pichia*, and fungi of the dematioid genus *Torula*.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Additives
Antibiotics

While it is generally preferred to have a high sugar concentration in the saccharified solution, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

Surfactants

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants. Other suitable surfactants include octylphenol ethoxylates such as the TRITON™ X series nonionic surfactants commercially available from Dow Chemical. A surfactant can also be added to keep the sugar that is being produced in solution, particularly in high concentration solutions.

Saccharification Medium

In one embodiment, the medium has the following concentrations of components:

| | |
|---|---|
| Yeast nitrogen base | 1.7 g/L |
| Urea | 2.27 g/L |
| Peptone | 6.56 g/L |
| Tween ® 80 surfactant | 10 g/L |

Physical Treatment of Feedstock
Physical Preparation

In some cases, methods can include a physical preparation, e.g., size reduction of materials, such as by cutting, grinding, shearing, pulverizing or chopping. For example, in other cases, material is first pretreated or processed using one or more of the methods described herein, such as radiation, sonication, oxidation, pyrolysis or steam explosion, and then size reduced or further size reduced. Treating first and then size reducing can be advantageous. Screens and/or magnets can be used to remove oversized or undesirable objects such as, for example, rocks or nails from the feed stream. In some cases no pre-processing is necessary, for example when the initial recalcitrance of the biomass is low, and wet milling is sufficiently effective to reduce the recalcitrance, for example, to prepared the material for further processing, e.g., saccharification.

Feed preparation systems can be configured to produce streams with specific characteristics such as, for example, specific maximum sizes, specific length-to-width, or specific surface areas ratios. Physical preparation can increase the rate of reactions or reduce the processing time required by opening up the materials and making them more accessible to processes and/or reagents, such as reagents in a solution. The bulk density of feedstocks can be controlled (e.g., increased). In some situations, it can be desirable to prepare a high or higher bulk density material, e.g., by densifying the material (e.g., densification can make it easier and less costly to transport to another site) and then reverting the material to a lower bulk density state. The material can be densified, for example from less than 0.2 g/cc to more than 0.9 g/cc (e.g., less than 0.3 to more than 0.5 g/cc, less than 0.3 to more than 0.9 g/cc, less than 0.5 to more than 0.9 g/cc, less than 0.3 to more than 0.8 g/cc, less than 0.2 to more than 0.5 g/cc). For example, the material can be densified by the methods and equipment disclosed in U.S. Pat. No. 7,932,065 and WO 2008/073186, the full disclosures of which are incorporated herein by reference. Densified materials can be processed by any of the methods described herein, or any material processed by any of the methods described herein can be subsequently densified. In some cases, the material can be densified prior to wet milling. Wet milling can re-open densified material.

Size Reduction

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less (1/16 inch, 0.0625 inch), provide a second fibrous material. If desired, the fiber source can be cut prior to the shearing, e.g., with a shredder. For example, when a paper is used as the fiber source, the paper can be first cut into strips that are, e.g., ¼- to ½-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source. The shredded fiber source In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, freezer milling, blade milling, knife milling, disk milling, roller milling or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The fiber cellulosic or lignocellulosic material can also be mechanically treated under a gas (such as a stream or atmosphere of gas other than air), e.g., oxygen or nitrogen, or steam.

If desired, lignin can be removed from any of the fibrous materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific morphology characteristics such as, for example, surface area, porosity, bulk density, and, in the case of fibrous feedstocks, fiber characteristics such as length-to-width ratio.

In some embodiments, a BET surface area of the mechanically treated material is greater than 0.1 m$^2$/g, e.g., greater than 0.25 m$^2$/g, greater than 0.5 m$^2$/g, greater than 1.0 m$^2$/g, greater than 1.5 m$^2$/g, greater than 1.75 m$^2$/g, greater than 5.0 m$^2$/g, greater than 10 m$^2$/g, greater than 25 m$^2$/g, greater than 35 m$^2$/g, greater than 50 m$^2$/g, greater than 60 m$^2$/g, greater than 75 m$^2$/g, greater than 100 m$^2$/g, greater than 150 m$^2$/g, greater than 200 m$^2$/g, or even greater than 250 m$^2$/g.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, after mechanical treatment the material has a bulk density of less than 0.25 g/cm$^3$, e.g., 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the fibrous materials mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the second feedstock is a fibrous material 14 the average length-to-diameter ratio of fibers of the mechanically treated material can be, e.g. greater than 8/1, e.g., greater than 10/1, greater than 15/1, greater than 20/1, greater than 25/1, or greater than 50/1. An average fiber length of the mechanically treated material 14 can be, e.g., between about 0.5 mm and 2.5 mm, e.g., between about 0.75 mm and 1.0 mm, and an average width (e.g., diameter) of the second fibrous material 14 can be, e.g., between about 5 μm and 50 μm, e.g., between about 10 μm and 30 μm.

In some embodiments, if the feedstock is a fibrous material, the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

Treatment to Solubilize, Reduce Recalcitrance or Functionalize

Materials that have or have not been physically prepared can be treated for use in any production process described herein. One or more of the production processes described below may be included in the recalcitrance reducing operating unit discussed above. Alternatively, or in addition, other processes for reducing recalcitrance may be included.

Treatment processes utilized by the recalcitrance reducing operating unit can include one or more of irradiation, sonication, oxidation, pyrolysis or steam explosion. Treatment methods can be used in combinations of two, three, four, or even all of these technologies (in any order).

Radiation Treatment

One or more radiation processing sequences can be used to process materials from the feedstock, and to provide a wide variety of different sources to extract useful substances from the feedstock, and to provide partially degraded structurally modified material which functions as input to further processing steps and/or sequences. Irradiation can, for example, reduce the molecular weight and/or crystallinity of feedstock. Radiation can also sterilize the materials, or any media needed to bioprocess the material.

In some embodiments, energy deposited in a material that releases an electron from its atomic orbital is used to irradiate the materials. The radiation may be provided by (1) heavy charged particles, such as alpha particles or protons, (2) electrons, produced, for example, in beta decay or electron beam accelerators, or (3) electromagnetic radiation, for example, gamma rays, x rays, or ultraviolet rays. In one approach, radiation produced by radioactive substances can be used to irradiate the feedstock. In some embodiments, any combination in any order or concurrently of (1) through (3) may be utilized. In another approach, electromagnetic radiation (e.g., produced using electron beam emitters) can be used to irradiate the feedstock. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Pat. No. 7,931,784, the full disclosure of which is incorporated herein by reference.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or a product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol. Radiation can also sterilize the materials or any media needed to bioprocess the material.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy" Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm. In some cases, multiple electron beam devices (e.g., multiple heads, often referred to as "horns") are used to deliver multiple doses of electron beam radiation to the material. This high total beam power is usually achieved by utilizing multiple accelerating heads. For example, the electron beam device may include two, four, or more accelerating heads. As one example, the electron beam device may include four accelerating heads, each of which has a beam power of 300 kW, for a total beam power of 1200 kW. The use of multiple heads, each of which has a relatively low beam power, prevents excessive temperature rise in the material, thereby preventing burning of the material, and also increases the uniformity of the dose through the thickness of the layer of material. Irradiating with multiple heads is disclosed in U.S. application Ser. No. 13/276,192 filed Oct. 18, 2011, the complete disclosure of which is incorporated herein by reference.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin piles of materials, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy. In a some embodiments energies between 0.25-10 MeV (e.g., 0.5-0.8 MeV, 0.5-5 MeV, 0.8-4 MeV, 0.8-3 MeV, 0.8-2 MeV or 0.8-1.5 MeV) can be used.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ Hz, greater than $10^{17}$ Hz, $10^{18}$, $10^{19}$, $10^{20}$, or even greater than $10^{21}$ Hz. In some embodiments, the electromagnetic radiation has a frequency of between $10^{18}$ and $10^{22}$ Hz, e.g., between $10^{19}$ to $10^{21}$ Hz.

Doses

In some embodiments, the irradiating (with any radiation source or a combination of sources) is performed until the material receives a dose of at least 0.25 Mrad, e.g., at least 1.0, 2.5, 5.0, 8.0, 10, 15, 20, 25, 30, 35, 40, 50, or even at least 100 Mrad. In some embodiments, the irradiating is performed until the material receives a dose of between 1.0 Mrad and 6.0 Mrad, e.g., between 1.5 Mrad and 4.0 Mrad, 2 Mrad and 10 Mrad, 5 Mrad and 20 Mrad, 10 Mrad and 30 Mrad, 10 Mrad and 40 Mrad, or 20 Mrad and 50 Mrad.

In some embodiments, the irradiating is performed at a dose rate of between 5.0 and 1500.0 kilorads/hour, e.g., between 10.0 and 750.0 kilorads/hour or between 50.0 and 350.0 kilorads/hours.

In some embodiments, two or more radiation sources are used, such as two or more ionizing radiations. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light.

Sonication, Pyrolysis and Oxidation

In addition to radiation treatment, the feedstock may be treated with any one or more of sonication, pyrolysis and oxidation. These treatment processes are described in U.S. Ser. No. 12/417,840 filed Apr. 3, 2009, the disclosure of which is incorporated by reference herein.

Other Processes to Solubilize, Reduce Recalcitrance or to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid), and/or base treatment (e.g., treatment with lime or sodium hydroxide)), UV treatment, screw extrusion treatment, solvent treatment (e.g., treatment with ionic liquids) and freeze milling. Some of these processes, for example, are described in U.S. Ser. No. 12/417,723 filed Apr. 3, 2009; Ser. No. 13/099,151 filed May 2, 2011; and Ser. No. 12/502,629 filed Jul. 14, 2009, the disclosures of which are incorporated herein.

Production of Fuels, Acids, Esters, and/or Other Products

After one or more of the processing steps discussed above have been performed on the biomass, the complex carbohydrates contained in the cellulose and hemicellulose fractions can be processed into fermentable sugars using a saccharification process, as discussed above.

After the resulting sugar solution has been transported to a manufacturing facility, the sugars can be converted into a variety of products, such as alcohols, e.g., ethanol, or organic acids. The product obtained depends upon the microorganism utilized and the conditions under which the bioprocessing occurs. These steps can be performed, for example, utilizing the existing equipment of the corn-based ethanol manufacturing facility.

The mixing processes and equipment discussed herein may also be used during bioprocessing, if desired. Advantageously, the mixing systems described herein do not impart high shear to the liquid, and do not significantly raise the overall temperature of the liquid. As a result, the microorganisms used in bioprocessing are maintained in a viable condition throughout the process. Mixing may enhance the reaction rate and improve the efficiency of the process.

Generally, fermentation utilizes various microorganisms. The sugar solution produced by saccharification of lignocellulosic materials will generally contain xylose as well as glucose. It may be desirable to remove the xylose, e.g., by chromatography, as some commonly used microorganisms (e.g., yeasts) do not act on xylose. The xylose may be collected and utilized in the manufacture of other products, e.g., animal feeds and the sweetener Xylitol. The xylose may be removed prior to or after delivery of the sugar solution to the manufacturing facility where fermentation will be performed.

The microorganism can be a natural microorganism or an engineered microorganism, e.g., any of the microorganisms discussed in the Materials section herein.

The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Carboxylic acid groups generally lower the pH of the fermentation solution, tending to inhibit fermentation with some microorganisms, such *Pichia stipitis*. Accordingly, it is in some cases desirable to add base and/or a buffer, before or during fermentation, to bring up the pH of the solution. For example, sodium hydroxide or lime can be added to the fermentation medium to elevate the pH of the medium to range that is optimum for the microorganism utilized.

Fermentation is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2 or 1 Mrad. In specific instances, the growth medium is treated with a dose of between about 1 and 3 Mrad.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

Mobile fermentors can be utilized, as described in U.S. Ser. No. 12/374,549 filed Jan. 21, 2009, now Published International Application No. WO 2008/011598. Similarly, the saccharification equipment can be mobile. Further, saccharification and/or fermentation may be performed in part or entirely during transit.

Post-Processing

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

Using the processes described herein, the treated biomass can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols, e.g., containing greater than 10%, 20%, 30% or even greater than 40% water, xylitol, biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha, beta unsaturated acids, such as acrylic acid and olefins, such as ethylene. Other alcohols and alcohol derivatives include propanol, propylene glycol, 1,4-butanediol, 1,3-propanediol, sugar alcohols (e.g., erythritol, glycol, glycerol, sorbitol threitol, arabitol, ribitol, mannitol, dulcitol, fucitol, iditol, isomalt, maltitol, lactitol, xylitol and other polyols), methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, γ-hydroxybutyric acid, and mixture thereof, a salt of any of these acids, or a mixture of any of the acids and their respective salts. a salt of any of the acids and a mixture of any of the acids and respective salts.

Other intermediates and products, including food and pharmaceutical products, are described in U.S. Ser. No. 12/417,900 filed Apr. 3, 2009, the full disclosure of which is hereby incorporated by reference herein.

Other Embodiments

A number of embodiments have been described. Nevertheless, it will be understood that various modifications may be made without departing from the spirit and scope of the disclosure.

In some implementations, the systems discussed herein, or components of these systems, may be portable, e.g., in the manner of the mobile processing equipment described in U.S. Ser. No. 12/374,549 filed Jun. 2, 2009 and International Application No. WO 2008/011598, the full disclosures of which are incorporated herein by reference.

While tanks have been referred to herein, the process may take place in any type of vessel or container, including lagoons, pools, ponds and the like. If the container in which mixing takes place is an in-ground structure such as a lagoon, it may be lined. The container may be covered, e.g., if it is outdoors, or uncovered.

In an alternate embodiment, the dispersing system 134 can be omitted in the systems shown in FIGS. 2A and 2B, and a pump can be used to draw liquid from the tank and deliver it through outlet pipe 137 to wet the feedstock material, which is then dispersed by the mixing action of the jet mixer 144. In such implementations, the pump would preferably be a low shear pump, e.g., a positive displacement pump such as the progressive cavity pumps available from SEEPEX and lobe pumps from Waukesha. It is also preferred that the pump be capable of pumping high viscosity fluids, since the viscosity of the liquid will increase as more feedstock is added.

While biomass feedstocks have been described herein, other feedstocks and mixtures of biomass feedstocks with other feedstocks may be used. For example, some implementations may utilize mixtures of biomass feedstocks with hydrocarbon-containing feedstocks such as those disclosed in U.S. Ser. No. 13/293,985 filed Nov. 10, 2011, the full disclosure of which is incorporated by reference herein.

Accordingly, other embodiments are within the scope of the following claims.

What is claimed is:

1. A method to process lignocellulosic material, the method comprising:
    irradiating the lignocellulosic material to produce irradiated lignocellulosic material having reduced recalcitrance; and
    wet milling the irradiated lignocellulosic material in a vessel while applying a jet mixer to the irradiated lignocellulosic material, using a wet milling system comprising one or more jet mixers and one or more wet mills, wherein one or more jet heads and one or more wet milling heads are disposed in a tank containing a fluid having the irradiated lignocellulosic material dispersed therein.

2. The method of claim 1 wherein the irradiating is by electron beam irradiation.

3. The method of claim 1 wherein the irradiating is by particle beam irradiation.

4. The method of claim 1 wherein the lignocellulosic material is selected from the group consisting of wood, particle board, sawdust, agriculture waste, sewage, silage, grasses, cotton, jute, hemp, flax, bamboo, sisal, abaca, corn cobs, switchgrass, hay, seaweed, algae, and mixtures thereof.

5. The method of claim 4 wherein the agricultural waste is selected from the group consisting of: rice hulls, bagasse, straw, corn stover and coconut hair.

6. The method of claim 4 wherein the silage is alfalfa.

7. The method of claim 1 further comprising densifying the irradiated lignocellulosic material prior to wet milling.

8. The method of claim 1 wherein wet milling is performed using a rotor/stator head comprising a rotor and a stator.

9. The method of claim 8 wherein the rotor and the stator include nesting rings of teeth.

10. The method of claim 9 wherein the stator comprises two or more concentric rings of teeth.

11. The method of claim 9 wherein the rotor comprises a ring of teeth configured to fit between adjacent rings of teeth of the stator.

12. The method of claim 8 wherein the clearance between the rotor and the stator is from about 0.01 inches to about 0.25 inches.

13. The method of claim 9 wherein the spacing between the teeth in each ring of teeth is from about 0.1 inch to about 0.3 inch.

14. The method of claim 1 wherein wet milling is performed using a plurality of rotor/stator heads.

15. The method of claim 1 wherein wet milling is performed at a shear rate of from about 30,000 $\sec^{-1}$ to about 50,000 $\sec^{-1}$.

16. The method of claim 1 wherein wet milling is performed in-line.

17. The method of claim 1 wherein wet milling is performed as a batch process.

18. The method of claim 1 further comprising adding an enzyme to the lignocellulosic material after wet milling.

19. The method of claim 18 further comprising adding a microorganism to the lignocellulosic material or to sugar derived from the lignocellulosic material.

20. The method of claim 19 wherein the microorganism is added after wet milling has been completed.

21. The method of claim 19 wherein the microorganism converts the lignocellulosic feedstock or the sugar to a product selected from the group consisting of alcohols, organic acids, sugars, hydrocarbons, and mixtures thereof.

22. The method of claim 21 wherein a jet mixer is operated during conversion of the feedstock or the sugar to the product.

* * * * *